(12) United States Patent
Lee et al.

(10) Patent No.: US 8,894,206 B2
(45) Date of Patent: Nov. 25, 2014

(54) AUTO-FOCUSING DIAGNOSTIC EQUIPMENT

(71) Applicant: Industrial Technology Research Institute, Hsinchu (TW)

(72) Inventors: Yuan-Chin Lee, Hsinchu (TW); Rung-Ywan Tsai, Taoyuan County (TW); Chi-Shen Chang, Zhubei (TW); Tai-Ting Huang, Hsinchu (TW); Hung-Yueh Chen, Taichung (TW); Hong-Chou Lyu, Changhua (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/727,664

(22) Filed: Dec. 27, 2012

(65) Prior Publication Data

US 2013/0169931 A1 Jul. 4, 2013

(30) Foreign Application Priority Data

Dec. 29, 2011 (TW) .............................. 100149644 A
Oct. 24, 2012 (CN) .......................... 2012 1 0411541

(51) Int. Cl.
*A61B 3/14* (2006.01)
*A61B 3/12* (2006.01)
*G02B 7/28* (2006.01)

(52) U.S. Cl.
CPC ... *A61B 3/12* (2013.01); *A61B 3/14* (2013.01); *G02B 7/28* (2013.01)
USPC ....................................................... 351/206

(58) Field of Classification Search
USPC .......... 351/205, 206, 210, 221; 356/450–456, 356/477–479; 382/131; 600/407, 425
See application file for complete search history.

(56) References Cited

U.S. PATENT DOCUMENTS

| 5,070,883 A | 12/1991 | Kasahara |
| 5,663,781 A | 9/1997 | Wilms et al. |

(Continued)

FOREIGN PATENT DOCUMENTS

| CN | 1901833 | 1/2007 |
| CN | 101365932 | 2/2009 |

(Continued)

OTHER PUBLICATIONS

English abstract translation of TW201014571 (Published Apr. 16, 2010).

(Continued)

*Primary Examiner* — Mahidere Sahle
(74) *Attorney, Agent, or Firm* — McClure, Qualey & Rodack, LLP

(57) ABSTRACT

A diagnostic equipment having an auto-focusing function comprising a image detection device, a first scanning device, a mobile optical lens assembly, a focusing detection device and a first splitter assembly is provided. The image detection device comprises a first light source and a first photo detector. The first light source provides a first incident light and the first incident light incident to an object and becomes a first signal light. The first photo detector is for receiving the first signal light. The first scanning device is for adjusting a path of the first incident light and to scan the object. The mobile optical lens assembly has a lens and a mobile platform. The first splitter assembly is for transmitting the first and the second signal light to the first and the second photo detector, respectively.

33 Claims, 32 Drawing Sheets

(56) References Cited

U.S. PATENT DOCUMENTS

| | | |
|---|---|---|
| 5,943,109 A | 8/1999 | Kim |
| 5,975,697 A * | 11/1999 | Podoleanu et al. ............ 351/206 |
| 6,004,314 A | 12/1999 | Wei et al. |
| 6,027,216 A | 2/2000 | Guyton et al. |
| 7,140,730 B2 | 11/2006 | Wei et al. |
| 7,368,207 B2 | 5/2008 | Rivers et al. |
| 7,445,335 B2 | 11/2008 | Su et al. |
| 7,542,951 B1 | 6/2009 | Chakrabarti et al. |
| 7,802,884 B2 | 9/2010 | Feldon et al. |
| 7,854,510 B2 | 12/2010 | Verdooner et al. |
| 8,071,929 B2 | 12/2011 | Sato et al. |
| 2001/0025226 A1 | 9/2001 | Lavery |
| 2005/0187465 A1 | 8/2005 | Motomura et al. |
| 2006/0203330 A1 | 9/2006 | Moeller et al. |
| 2007/0013867 A1 | 1/2007 | Ichikawa |
| 2007/0231717 A1 | 10/2007 | Rivers et al. |
| 2007/0288795 A1 | 12/2007 | Leung et al. |
| 2008/0118886 A1 | 5/2008 | Liang et al. |
| 2010/0103372 A1 | 4/2010 | Bille |
| 2012/0147212 A1* | 6/2012 | Hara et al. ................. 348/223.1 |

FOREIGN PATENT DOCUMENTS

| | | |
|---|---|---|
| CN | 101556373 | 10/2009 |
| CN | 101564286 | 10/2009 |
| TW | 200630068 A | 9/2006 |
| TW | I292706 | 1/2008 |
| TW | 200806258 A | 2/2008 |
| TW | 201014571 | 4/2010 |

OTHER PUBLICATIONS

English abstract translation of TWI292706 (Published Jan. 21, 2008).
English abstract translation of CN1901833 (Published Jan. 24, 2007).
English abstract translation of CN101564286 (Published Oct. 28, 2009).
Lo, et al.: "Fiber type of optical coherence tomography with an auto-focus device"; 0030-4018/$—see front matter © 2005 Elsevier B.V. All rights reserved. doi:10.1016/j.optcom.2005.08.050.
"Competence between spatial and temporal coherence in full field optical coherence tomography and interference microscopy"; 1464-4258/06/110952+07$30.00 © 2006 IOP Publishing Ltd Printed in the UK; (http://iopscience.iop.org/1464-4258/8/11/004).
Lo, et al.: "Fiber Type of Optical Coherence Tomography with Auto-Focus Design"; 17th International Conference on Optical Fibre Sensors, Marc Voet, Reinhardt Willsch, Wolfgang Ecke, Julian Jones, Brian Culshaw, eds., Proceedings of SPIE vol. 5855 (SPIE, Bellingham, WA, 2005)—0277-786X/05/$15—doi: 10.1117/12.623873. (Aug. 30, 2005).
Boppart, et al.: "Optical coherence tomography: feasibility for basic research and image-guided surgery of breast cancer"; Breast Cancer Research and Treatment 84: 85-97, 2004. © 2004 Kluwer Academic Publishers. Printed in the Netherlands.
Wei, et al.: "Optical Coherence Tomography in Ophthalmic Applications"; Light-Emitting Diodes: Research, Manufacturing, and Applications VII, E. Fred Schubert, H. Walter Yao, Kurt J. Linden, Daniel J. McGraw, Editors, Proceedings of SPIE vol. 4996 (2003).
TW Office Action dated Mar. 6, 2014.
CN Office Action dated Jul. 24, 2014.

* cited by examiner

12C

12D

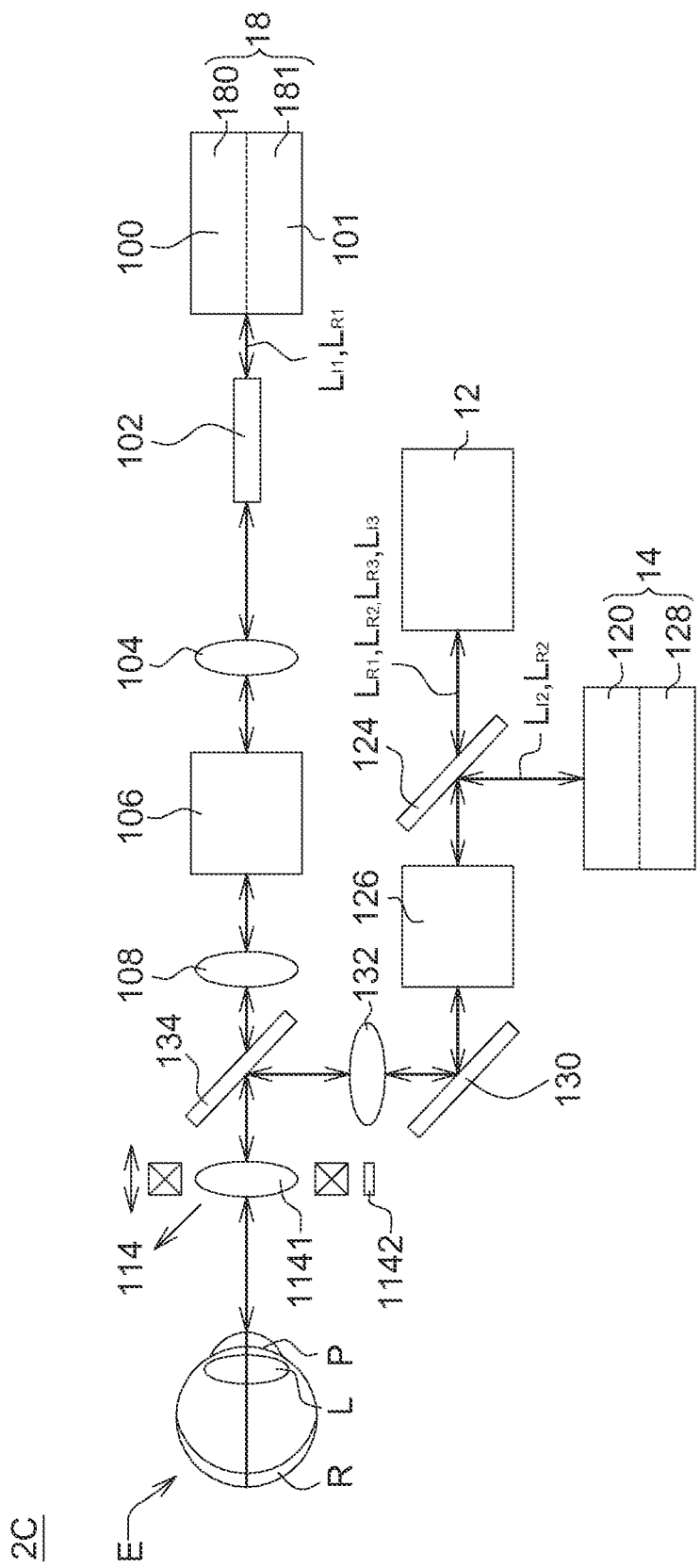

IMA 0.000 0.000 NM

IMA 0.000 0.000 NM

IMA 0.000 0.000 NM

AUTO-FOCUSING DIAGNOSTIC EQUIPMENT

This application claims the benefit of Taiwan application Serial No. 100149644, filed Dec. 29, 2011, as well as the People's Republic of China application Serial No. 201210411541.4, filed Oct. 24, 2012, the subject matters of which are incorporated herein by reference.

TECHNICAL FIELD

The disclosure relates in general to a diagnostic equipment of an ophthalmology, and more particularly to a diagnostic equipment of an ophthalmology having an auto-focusing function.

BACKGROUND

Currently, an ophthalmology diagnostic equipment can not only detect the eye function, but also investigate the lesions status of the cornea, the anterior chamber, the eye lens, the retina and the optic nerve through the cornea scan, the anterior chamber scan, the eye lens scan, the fundus tomography and structure analysis.

Anterior chamber is a room between the cornea and the iris. The anterior chamber is full of aqueous humour. The vascular permeability of the iris can be increased when the eye is injured, or blood accumulates at the anterior chamber because of the blood vessel ruptured and bleeding. Blood accumulated at the anterior chamber is referred to as post-injury anterior chamber bleeding. Generally speaking, post-injury anterior chamber bleeding most commonly results from contusion of eyeball. A small portion of post-injury anterior chamber bleeding result from intraocular tumor, neovascular glaucoma, etc. The pathogenesis can be determined by using anterior chamber mirror for examination. The optical disease can be detected and analyzed, if the an image of fundus can be provided by using fundus tomography and fundoscope, so that the doctor can anticipate the optical disease earlier and provide better estimation prior the treatment and exam the status of prognosis.

Before optic examination such as anterior chamber scan or fundus tomography, the head of a patient should be relied on a headrest as a lead action of optic tomography or fundus image detection, so that the head of the patient is relatively stable. Then, the doctor can find the find the eye tissue (such as anterior chamber) or image of fundus, and plan a path mode of the tomography for correlated examination of tomography and analysis manually.

However, the doctor needs to re-focus the eyes of different patient when examining different patient. Moreover, the doctor needs to adjust the system again, if the patient moves his head. It is inconvenient that the doctor should adjust the system again when re-examination, if the patient takes a break or moves his head during the lengthy examination.

SUMMARY

The disclosure is directed to a diagnostic equipment of an ophthalmology having an auto-focusing function. By utilizing the focusing detection device to detect the light reflected by the eye tissue of the patient automatically, the focal length can be adjusted in favor of the examining of the eyes.

According to an aspect of the present disclosure, a diagnostic equipment having an auto-focusing function comprising an image detection device, a first scanning device, a mobile optical lens assembly, a focusing detection device and a first splitter assembly is provided. The image detection device comprises a first light source and a first photo detector. The first light source provides a first incident light, and the first incident light incident to an object and becomes a first signal light. The first photo detector is used for receiving the first signal light. The first scanning device is used for adjusting a path of the first incident light and to scan the object. The mobile optical lens assembly has a lens and a mobile platform for carrying the lens. The first splitter assembly used for transmitting the first signal light to the first photo detector and transmitting the second signal light to the second photo detector. The focusing detection device comprises a second photo detector, a focusing error produce assembly and a controlling unit. The second photo detector is used for detecting a second signal light reflected by the object. The focusing error produce assembly is disposed between the second photo detector and the mobile optical lens assembly. The controlling unit is electrical connected to the second photo detector and the mobile platform to control a movement of the mobile platform and adjust a focusing position of the first incident light according to a electric signal converted by the second signal light.

The above and other aspects of the disclosure will become better understood with regard to the following detailed description of the non-limiting embodiment(s). The following description is made with reference to the accompanying drawings.

BRIEF DESCRIPTION OF THE DRAWINGS

FIG. 5A~FIG. 5C illustrate a diagnostic equipment according to an embodiment of the disclosure;

DETAILED DESCRIPTION

The structure and working principles of embodiments of the disclosure are described below.

Figure 1A:
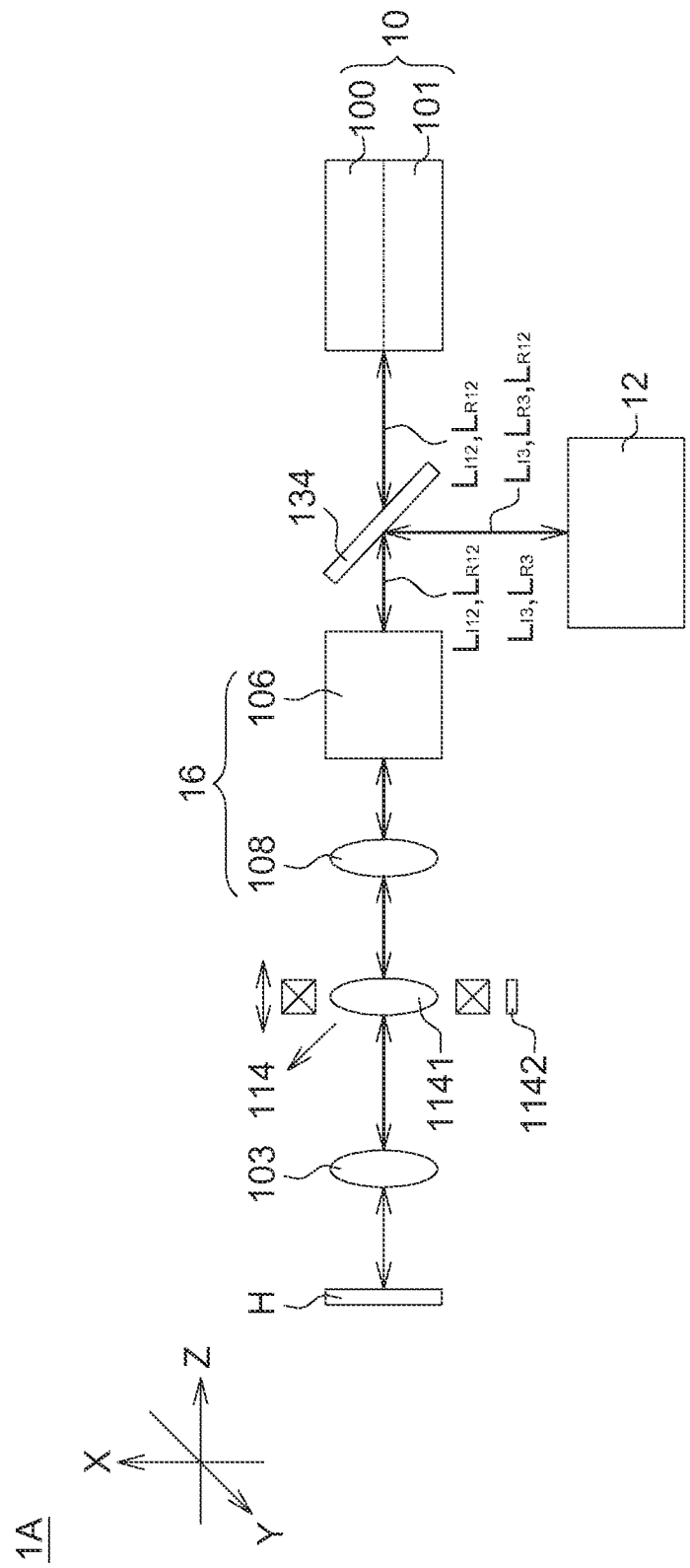
FIG. 1A~FIG. 1B illustrate a diagnostic equipment according to an embodiment of the disclosure.
Figure 1B:
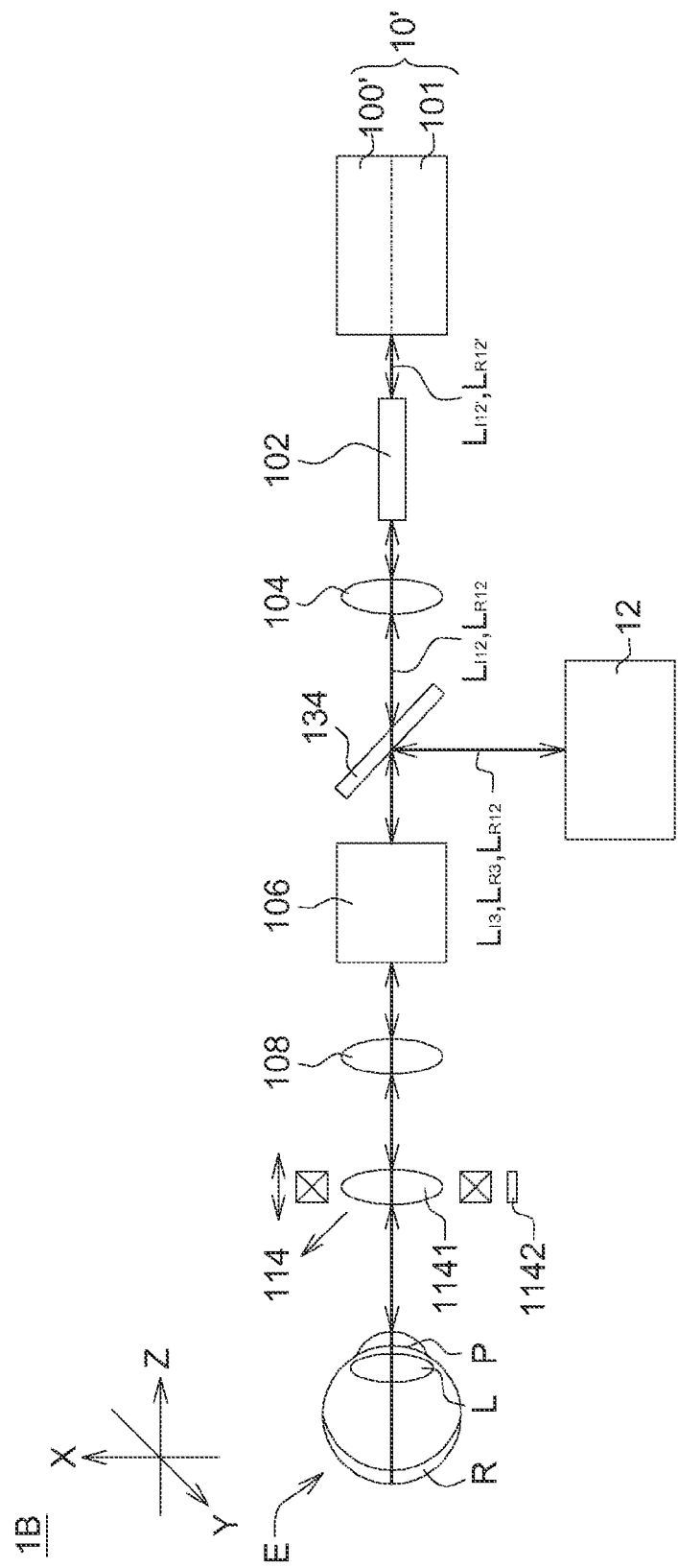

Please refers to FIG. 1A~FIG. 1B. FIG. 1A~FIG. 1B illustrate a diagnostic equipment 1A and a diagnostic equipment 1B according to an embodiment of the disclosure. As shown in FIG. 1A, the diagnostic equipment 1A comprise image detection device 10, focusing detection device 12, first splitter assembly 134, scan device 16, mobile optical lens assembly 114 and focusing lens 103. The first splitter assembly 134 can be a beam splitter, a splitting diffraction assembly, a splitter optical fiber assembly or a splitter waveform assembly. Scan device 16 comprises scan mirror 108 and scan assembly 106. The scan assembly 106 is for example a pair of galvano-meter scanning reflecting mirror. The image detection device 10 can be for example a tomography device and/or a fundoscope.

In this embodiment, the image detection device 10 comprises a light source 100 and a photo detector 101, the light source 100 is for example a collimating near-infrared light source, used for providing a light beam $L_{I12}$. The focusing detection device 12 is electrical connected to a mobile optical lens assembly 114. The mobile optical lens assembly 114 comprises lens 1141 and a mobile platform 1142 for carrying the lens 1141. The photo detector 101 is for example a charge coupling diode (CCD), a complementary metal-oxide semiconductor (CMOS), a positive intrinsic negative (PIN) detector or avalanche photo detector, etc. In other embodiments, the waveform ranges of the light source 100 can be selected according to the requirement and not limited to the near-infrared light source.

As shown in FIG. 1A, when the light beam passes through the first splitter assembly 134, the scan device 16, the mobile optical lens assembly 114 and the focusing lens 103, the light beam is incident to an object H and the light beam $L_{I12}$ is reflected by the object H and becomes a light beam $L_{R12}$. The scan device 16 is used for making the light beam incident to the object H scanning the object along X-Y plane. The first splitter assembly 134 is used for separate the light beam $L_{R12}$ into two light paths, the two light paths of the light beam $L_{R12}$ are incident to the photo detector 101 and the focusing detection device 12, respectively. As shown in FIG. 1A, the first splitter assembly 134 is for example a beam splitter. The beam splitter is for example a partially light-transmittable and partially light-reflectable beam splitter. The focusing detection device 12 receives the signal of the light beam $L_{R12}$, and then controls the movement of the mobile platform 1142 according to detected signal to adjust the focusing position of the light beam $L_{I12}$.

Please refer to FIG. 1B, merely differences between the diagnostic equipment 1B and the diagnostic equipment 1A are described herein. As shown in FIG. 1B, the diagnostic equipment 1B is for example a diagnostic equipment used in ophthalmology, and is used for detecting the eye tissue E. Therefore, the focusing lens 103 in FIG. 1A can be omitted. The light beam $L_{I12}$ passes through the mobile optical lens assembly 114, and then passes through the pupil of the eye tissue E, and then focuses at the eye lens L.

Besides, the image detection device 10' in FIG. 1B comprises a light source 100' and a photo detector 101. The light source 100' is for example a near-infrared light source without collimation, and is used for providing a light beam $L_{I12'}$. At this time, a optical fiber 102 and a first collimating mirror 104 can be disposed between the light source 100' and the first splitter assembly 134, for collimating the light beam $L_{I12'}$ into light beam $L_{I12}$, the collimated light beam $L_{I12}$ passes through the scan assembly 106, and then passes from the scan mirror 108 to the mobile optical lens assembly 114. Then, the collimated light beam $L_{I12}$ is incident to pupil P and then enters the eye tissue E, the light beam $L_{I12}$ is reflected by the eye tissue E and becomes the light beam $L_{R12}$. The first splitter assembly 134 is used for splitting the light beam $L_{R12}$ and respectively incident to the split light beam $L_{R12}$ to the focusing detection device 12 and image detection device 101. In this embodiment, the optical fiber 102 is for example a single mode optical fiber that is difficult to disperse. The light source 100 (such as a collimated near-infrared light source) in FIG. 1A can also be used to replace the light source 100', and thus the optical fiber 102 and the first collimating mirror 104 can be omitted.

In one embodiment, the image detection device 10 and/or the image detection device 10' can be a tomography device, such as a optical coherence tomography (OCT) device. In this case, the light source 100 and/or the light source 100' is for example a tomography light source, which comprises an interferometer and a reference light path. The tomography light source is for example a near-infrared light source with waveform ranges between 800 nm~1400 nm. The photo detector 101 is for example a spectrometer with a splitter assembly.

In one embodiment, the image detection device 10 and/or image detection device 10' can be a fundoscope, such as a scan laser ophthalmoscope (SLO). In this case, the light source 100 and/or light source 100' is for example a fundoscope light source. The fundoscope light source can be a near-infrared light source with waveform ranging from 780 nm to 830 nm. The photo detector 101 is for example an image module, used for converting the received signal light into an image signal and displaying the image signal on a display. In another one embodiment, the image detection device 10 and/or image detection device 10' can comprise the tomography device and the fundoscope simultaneously.

Figure 2A:
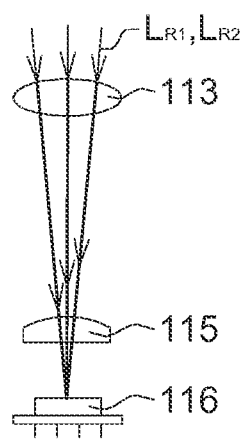
FIG. 2A~FIG. 2B illustrate a focusing detection device according to an embodiment of the disclosure.
Figure 2B:
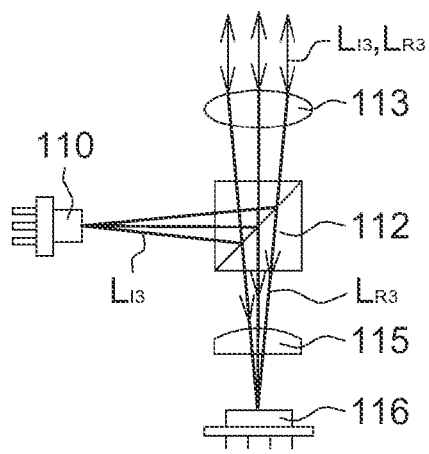

Please refers FIG. 2A~FIG. 2B. FIG. 2A~FIG. 2B illustrate the focusing detection device 12 in FIG. 1A~FIG. 1B. The focusing detection device 12A is a focusing detection device 12 of one embodiment in FIG. 1A~FIG. 1B. As shown in FIG. 2A, the focusing detection device 12A comprises a second collimating mirror 113, a focusing error produce assembly (such as a cylindrical lens) 115 and photo detector (PD) 116. The second collimating mirror 113 herein is a focusing lens and is used for focusing the light beam $L_{R1}$ or the light beam $L_{R2}$. In FIG. 2A, a typical focusing lens can be used to replace the second collimating mirror 113. In other embodiment, a fresnel lens or a binary optics lens can be used to replace the second collimating mirror 113. The photo detector 116 can be for example a quad detector. The cylindrical lens 115 is for example a cylinder shaped lens. The light beam passing through the cylindrical lens 115 can be focused on two focusing surfaces, and the optical points on the two focusing surfaces are two lines perpendicular to each other (one is a horizontal line and the other is vertical line). In another one embodiment, the focusing error produce assembly can also be a diffractive optical element (DOE). The diffractive optical element having functions of cylindrical lens 115 described in FIG. 2A~FIG. 2B can replaces the cylindrical lens 115 in FIG. 2A~FIG. 2B.

Please refer to both FIG. 1A~FIG. 1B and FIG. 2A, the focusing detection device 12A shares the light source with the image detection device 10 or image detection device 10'. When the image detection device 10 or image detection device 10' is a tomography device, the tomography light source is reflected by the object H or the eye tissue E and becomes the light beam $L_{R1}$. When image detection device 10 or image detection device 10' is a fundoscope, the fundoscope light source reflected by the object H or the eye tissue E and becomes the light beam $L_{R2}$. As shown in FIG. 2A, despite the image detection device 10 or image detection device 10' being a tomography device or a fundoscope, the light beam $L_{R1}$ or the light beam $L_{R2}$ returns along the original light path and passes through the first splitter assembly 134 to be split. A light path of the split light is incident to the photo detector 116 of the focusing detection device 12.

Please refers to FIG. 2B, the focusing detection device 12B is one implementation of the focusing detection device 12 in FIG. 1A~FIG. 1B. Please refer to both FIG. 1A and FIG. 2B, the difference between the focusing detection device 12B and the focusing detection device 12A in FIG. 2A is that the focusing detection device 12 B further comprises a light source 110 and a second splitter assembly 112. In embodiment of FIG. 2B, the second splitter assembly 112 is for example a square beam splitter. The light source 110 is for example a laser diode (PD). As shown in the embodiments of FIG. 1A and FIG. 2B, the light source 110 provides a light beam $L_{I3}$, the light beam $L_{I3}$ passes through the second splitter assembly 112 and is reflected to the second collimating mirror 113. The light beam $L_{I3}$ is collimated by the second collimating mirror 113 and is incident to the eye tissue E by the first splitter assembly 134. Then, the light beam $L_{I3}$ is reflected by the object H or the eye tissue E and becomes the light beam $L_{R3}$, and is incident to the second collimating mirror 113 along the original path. Then, the light beam $L_{I3}$ passes from the second splitter assembly 112 to the cylindrical lens 115, and is reflected to the photo detector 116. Since the focusing detection device 12B has an independent light source 110, the focusing detection device 12B does not share the light source with the image detection device 10. Therefore, the photo detector 116 receives the light beam $L_{R3}$ which is the light beam of the light source 110 being reflected by the object H or the eye tissue E. The second splitter assembly 112 is used to integrate the light beam $L_{I3}$ and light beam $L_{R3}$. In FIG. 2A and FIG. 2B, the cylindrical lens 115 is used to generate astigmatism, so that the light beam passed through the cylindrical lens 115 focused on two focusing surfaces, and the focusing points on the two focusing surface are two lines perpendicular to each other (a horizontal line and a vertical line). Therefore, a slant plate (not shown) can be used to achieve an effect of astigmatism. The slant plate can be mostly disposed at 45 degrees tilt. The slant plate can also be disposed at other degrees tilt such as degrees larger than 60 degrees or smaller than 30 degrees, and is not limited thereto. Assuming that the effect of astigmatism can be generated, the cylindrical lens 115 in FIG. 2A can be replaced by the plate described above. In FIG. 2B, when the slant plate having functions of splitting light as the second splitter assembly 112, the slant plate can replace the second splitter assembly 112 and cylindrical lens 115 directly. The light source 110 and the photo detector 116 are the same as that shown in FIG. 2B.

In one embodiment, the focusing detection device 12B in FIG. 2B can be replaced by two collimating mirrors (not illustrated) to replace the second collimating mirror 113. In particular, one of the collimating mirrors can be disposed between the light source 110 and the second splitter assembly 112, and another one collimating mirror can be disposed between the second splitter assembly 112 and the cylindrical lens 115. In this case, the second collimating mirror 113 of the focusing detection device 12B in FIG. 2B can be omitted. The reproduced focusing detection device can achieve same effect as the focusing detection device 12B in FIG. 2B.

Figure 3A:
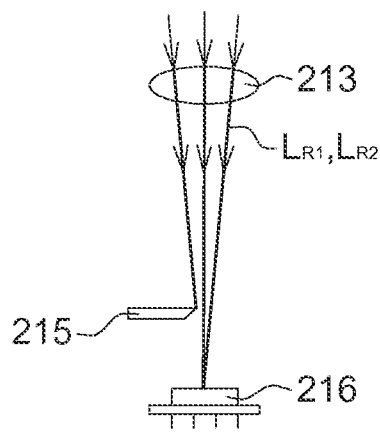
FIG. 3A~FIG. 3B illustrate a focusing detection device according to another one embodiment of the disclosure.
Figure 3B:
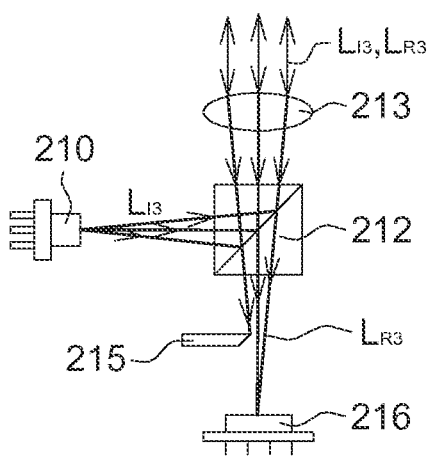

Please refers to FIG. 3A~FIG. 3B. FIG. 3A~FIG. 3B illustrate another one embodiment of the focusing detection device 12 in FIG. 1A~FIG. 1B. The focusing detection device 12C shown in FIG. 3A is another one embodiment of FIG. focusing detection device 12 in 1A~FIG. 1B. As shown in FIG. 3A, the focusing detection device 12C comprises a second collimating mirror 213, a focusing error produce assembly such as a blade 215 and a photo detector 216. The photo detector 216 is for example a binary detector. The blade 215 has a knife edge or a blade margin. The second collimating mirror 213 herein is used as focusing lens, for focusing the light beam $L_{R1}$ or the light beam $L_{R2}$. In FIG. 3A, an ordinary focusing lens can be used to replace the second collimating mirror 213. The light path of light beam $L_{R1}$ and light beam $L_{R2}$ in FIG. 3A and FIG. 2A are similar. Differences between the focusing detection device 12C and the focusing detection device 12A are that the focusing detection device 12C omits a cylindrical lens 115, and utilizes a blade 215 disposed between the second collimating mirror 213 and the photo detector 216. Besides, a knife edge or a blade margin of the blade 215 is used to cover half of the light beam $L_{R1}$ or light beam $L_{R2}$. In other embodiment, a fresnel lens, a diffractive optical element or a binary optics lens assembly can be used to replace the second collimating mirror 213 or the focusing error produce assembly.

Please refer to FIG. 1A and FIG. 3B, focusing detection device 12D can further comprise a light source 210 and a second splitter assembly 212 disposed between the second collimating mirror 213 and the blade 215, the second splitter assembly 212 for example is a partially transitive and partially reflective splitter assembly. As shown in FIG. 3B, the focusing detection device 12D has a independent light source 210 and does not need to share a light source with the image detection device 10, the light source 210 can provide a light beam $L_{I3}$, the light beam $L_{I3}$ is reflected by the object H or eye tissue E and becomes a reflected light beam $L_{R3}$. Therefore, the photo detector 216 receives the light beam $L_{R3}$. In some embodiments, the light beam $L_{I12}$ can be fluorescence or luminescence generated from the light beam $L_{I12}$ reflected by object H or eye tissue E, and is not limited to the reflected light reflected by the object.

In an embodiment of the focusing detection device 12D in FIG. 3B, the second collimating mirror 213 can be replaced by two collimating mirror (no shown). In particular, a collimating mirror can be disposed between the light source 210 and the second splitter assembly 212, and another one collimating mirror can be disposed between the second splitter assembly 212 and the blade 215. Besides, the second collimating mirror 213 of the focusing detection device 12D in FIG. 3B is omitted. In this case, the focusing detection device described above can achieve the same function as the focusing detection device 12D in FIG. 3B.

Figure 4A:
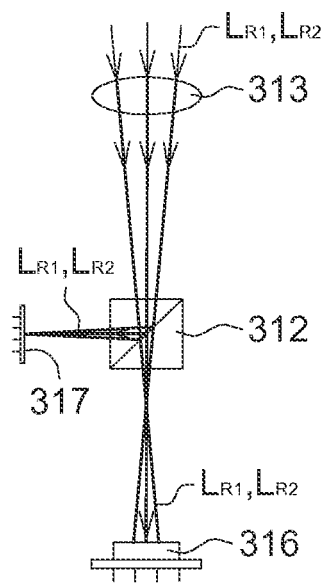
FIG. 4A~FIG. 4B illustrate a focusing detection device according to still another one embodiment of the disclosure.
Figure 4B:
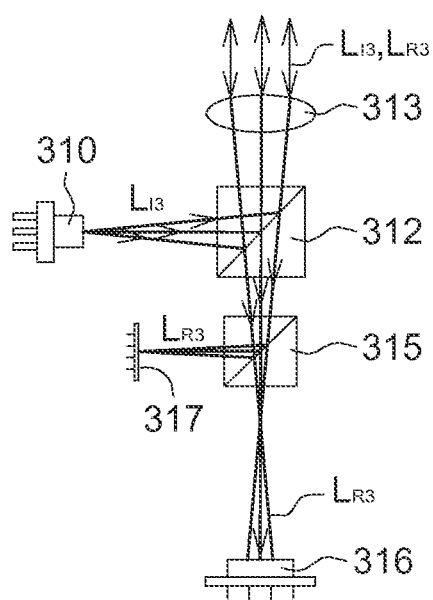

Please refers to FIG. 4A~FIG. 4B. FIG. 4A~FIG. 4B illustrate another embodiment of the focusing detection device 12 in FIG. 1A~FIG. 1B. As shown in FIG. 4A, the focusing detection device 12 E is another embodiment of the focusing detection device 12 in FIG. 1A~FIG. 1B. As shown in FIG. 4A, the focusing detection device 12E comprises a focusing error produce assembly such as a second splitter assembly 312 and a photo detector 317, a second collimating mirror 313 and a photo detector 316. The second collimating mirror 313 herein is used as a focusing lens, for focusing the light beam $L_{R1}$ or the light beam $L_{R2}$. In FIG. 3A, an ordinary focusing lens can also be used for replacing the second collimating mirror 313. The photo detector 316 and photo detector 317 for example are trisection detector. The second splitter assembly 312 for example is a partially transitive and partially reflective splitter assembly. The second splitter assembly 312 is used for splitting the light beam $L_{R1}$ or light beam $L_{R12}$ of the light source 100 reflected by the object H or eye tissue E and transmitting the split light beams to the photo detector 316 and photo detector 317, respectively.

As shown in FIG. 1A and FIG. 4B, the focusing detection device 12F further comprises a light source 310 and a third splitter assembly 315. The light source 310 for example is a lasing diode, the third splitter assembly 315 for example is a partially transitive and partially reflective splitter assembly. The light source 310 provides a light beam $L_{J3}$ passing through the second splitter assembly 312 and the second collimating mirror 313, and then incident to the object H or eye tissue E through the first splitter assembly 134. The light beam $L_{J3}$ is then reflected by the object H or eye tissue E and becomes the light beam $L_{R3}$. The light beam $L_{R3}$ is incident to the second collimating mirror 313, and is passing through the second splitter assembly 312 and third splitter assembly 315 along the original path, and then incident to the photo detector 316 and the photo detector 317.

In an embodiment, the second collimating mirror 313 can be replaced by two collimating mirror (not shown) in the focusing detection device 12F of FIG. 4B. In particular, one of the collimating mirrors can be disposed between the light source 310 and the second splitter assembly 312 and another one of the collimating mirrors can be disposed between the second splitter assembly 312 and the third splitter assembly 315. Besides, a second collimating mirror 313 of the focusing detection device 12F in FIG. 4B can be omitted. In this case, the focusing detection device described above can achieve the same function as the focusing detection device 12F in FIG. 4B.

As shown in FIG. 2A, FIG. 3A and FIG. 4A, the focusing detection device 12 described in the above embodiments can share the light source 100 with the image detection device 10. Since the light source and the second splitter assembly can be omitted in this case, the cost of the focusing detection device 12 can be decreased, and the size of the structure can be reduced. Besides, as shown in FIG. 2B, FIG. 3B and FIG. 4B, the focusing detection device 12 can comprise an independent light source. Therefore, the waveform of the independent light source can be different from the waveform of the light source 100. In this case, the light beam $L_{R3}$ reflected by the object H or eye tissue E can incident to the photo detector directly does not need to be split to the focusing detection device 12 and image detection device 10. Therefore, the photo detector can receives a stronger signal and the detecting error can be reduced.

Figure 5A:
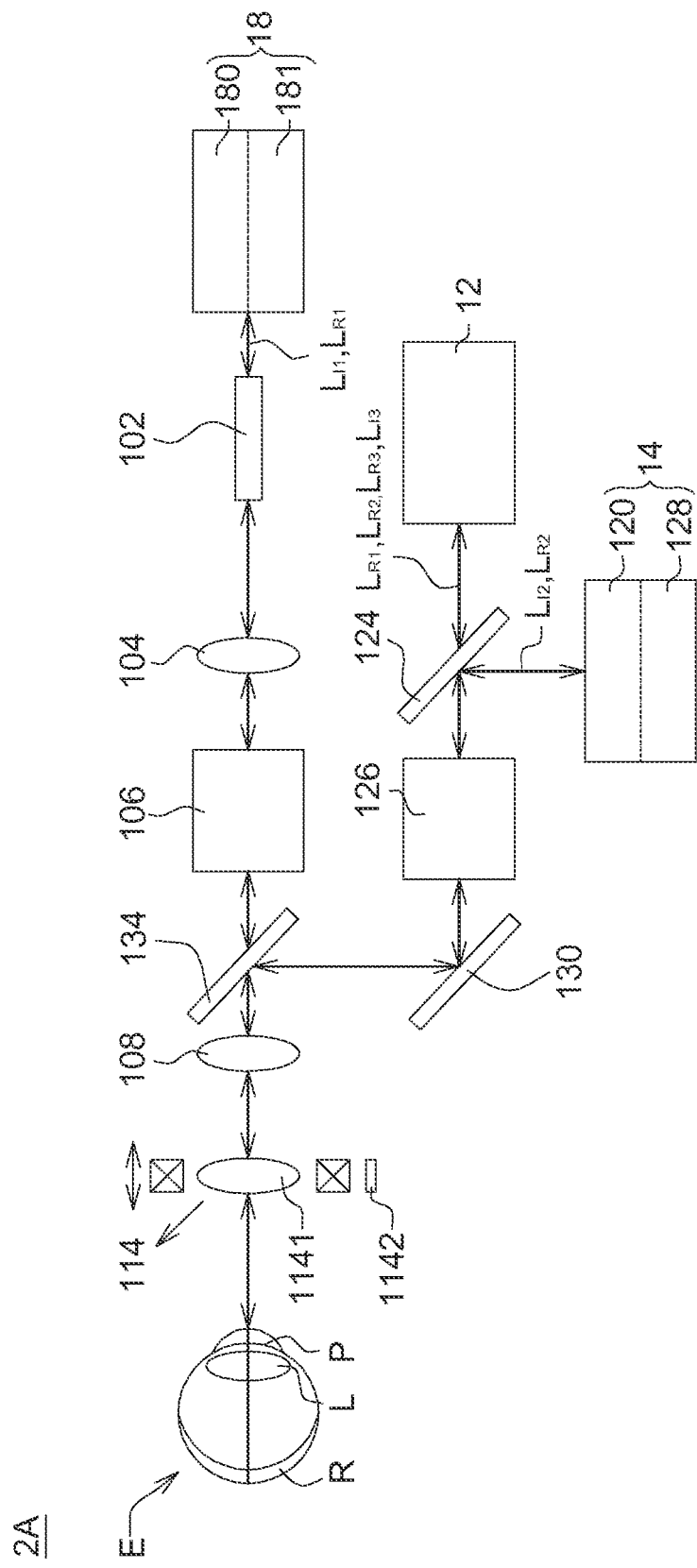
Figure 5B:
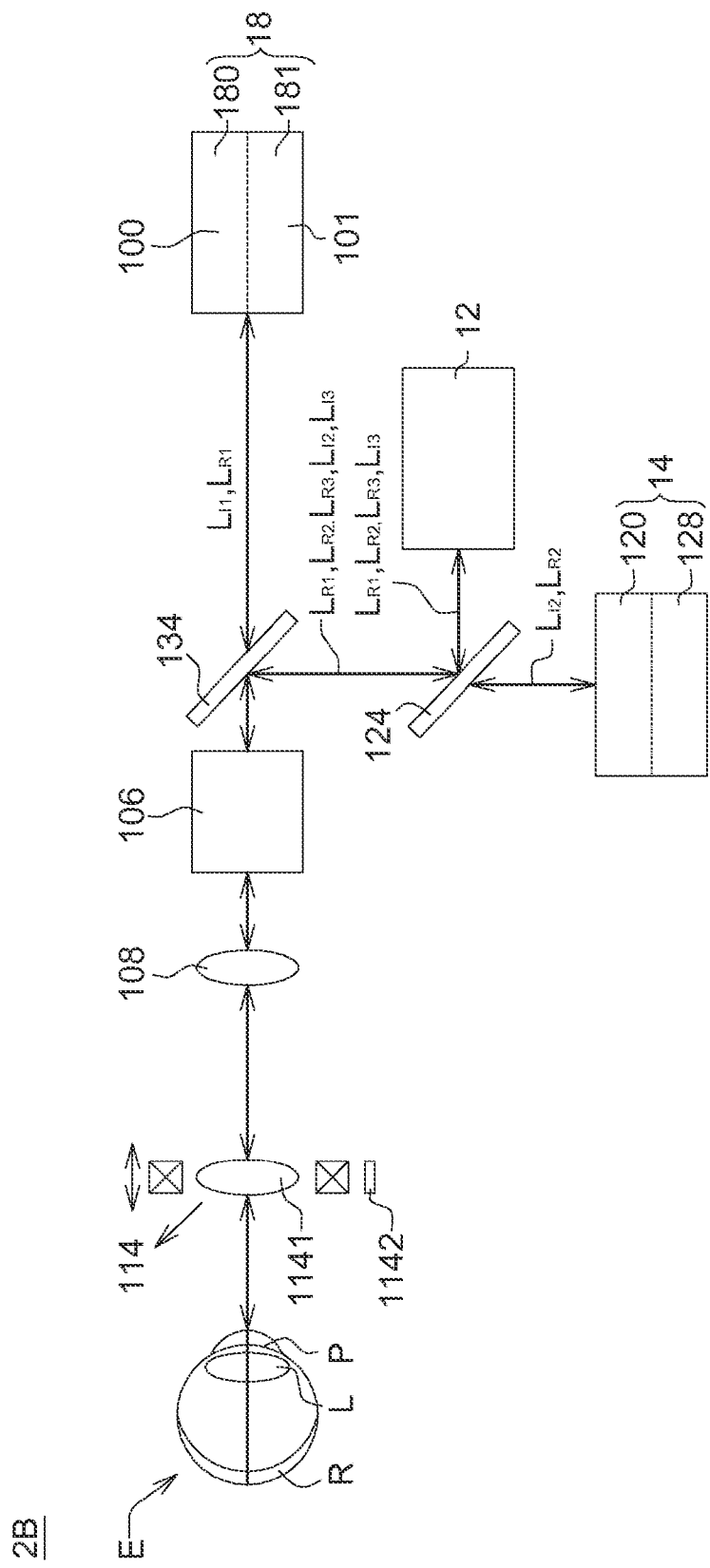

Please refers to FIG. 5A~FIG. 5C. FIG. 5A~FIG. 5C illustrates another one embodiment of the disclosure of the diagnostic equipment in FIG. 2A~2C. As shown in FIG. 5A, the diagnostic equipment 2A comprises a tomography device 18, a focusing detection device 12 and a fundoscope 14. The tomography device 18 comprises a tomography light source 180 and a photo detector 181. The tomography light source 180 for example is a near-infrared light source with wavelength ranges from 800 nm to 1400 nm and a reference light path, the photo detector 181 for example is a spectrometer with a splitter assembly. The tomography light source 180 is used for providing an emitting light beam $L_{J1}$. The optical fiber 102 and a first collimating mirror 104 can be selectively used according to a characteristic of the tomography light source 180. In other words, when the tomography light source 180 is a collimating light source, the optical fiber 102 and the first collimating mirror 104 can be omitted. Besides, the scan assembly 106, the scan mirror 108 and the mobile optical lens assembly 114 are the same as the corresponding components in FIG. 1A~FIG. 1B.

As shown in FIG. 5A, the fundoscope 14 comprises a light source 120 for providing the light beam $L_{J2}$, an image module 128 and a scan assembly 126. The image module 128 for example is a charge coupling diode, a CMOS, a PIN detector, or avalanche photo detector, used for converting the received light signal into electrical signals to display the scanning image of fundus. The fourth splitter assembly 124 is used for integrate the light path of the fundoscope 14 and the light path of the focusing detection device 12. In this embodiment, a position of the focusing detection device 12 and a position of the fundoscope 14 are interchangeable, if a light path of the focusing detection device 12 and a light path of the fundoscope 14 can be integrated by the fourth splitter assembly 124. The reflecting mirror 130 is used for reflecting the light source 120 of the fundoscope 14 and the light source of the focusing detection device 12 to the first splitter assembly 134. The first splitter assembly 134 is disposed between the scan mirror 108 and scan assembly 106, for integrating light paths of the light source 120 in the fundoscope 14, the light source in the focusing detection device 12 and the light source 180 in the tomography.

The focusing detection device 12 described herein in this embodiment is the same as the focusing detection device 12 in FIG. 1A~FIG. 1B. The focusing detection device 12 can be implemented by ways of the focusing detection device 12A~12F in FIG. 2A~FIG. 2B, FIG. 3A~FIG. 3B and FIG. 4A~FIG. 4B. In other words, the focusing detection device 12 in this embodiment can share the light source with the fundoscope 14 or the tomography device 18. At this time, the structure of the focusing detection device 12 are similar to the focusing detection devices in FIG. 2A, FIG. 3A and FIG. 4A. The focusing detection device 12 in this embodiment can comprise an independent light source, at this time, the structure of the focusing detection device 12 are similar to the focusing detection devices in FIG. 2B, FIG. 3B and FIG. 4B. Detail structures of the focusing detection device 12 are not described herein.

Please refers to FIG. 5B, the diagnostic equipment 2B comprises a tomography device 18, a focusing detection device 12 and a fundoscope 14. The diagnostic equipment 2B is similar to the diagnostic equipment 2A of FIG. 5A. Merely the difference between the diagnostic equipment 2B and the diagnostic equipment 2A are described herein. As shown in FIG. 5B, the first splitter assembly 134 is disposed between the tomography device 18 and the scan assembly 106, and is used for integrating the light path of the light source 120 of the fundoscope 14, the light source of the focusing detection device 12 and the light source 180 of the tomography. In this time, the tomography device 18 and the fundoscope 14 can share the scan assembly 106. Therefore, the scan assembly 126 and reflecting mirror 130 can be omitted.

Please refers to FIG. 5C, the diagnostic equipment 2C comprises the tomography device 18, the focusing detection device 12 and the fundoscope 14. The diagnostic equipment 2C is similar to the diagnostic equipment 2A in FIG. 5A. Merely the difference between the diagnostic equipment 2C and the diagnostic equipment 2A are described herein. As shown in FIG. 5C, the first splitter assembly 134 is disposed between the mobile optical lens assembly 114 and the scan mirror 108, for integrating the light source 120 of the fundoscope 14, focusing the light path of the light source of the detection device 12 and the light source 180 of the tomography. Besides, a scan mirror 132 is disposed between the reflecting mirror 130 and the first splitter assembly 134. The scan assembly 126 and scan mirror 132 are used to adjust the emitted light beam $L_{I2}$ of the light source 120 in the fundoscope 14 to scan the eye tissue E.

Based on the above, the diagnostic equipment 2A~2C described herein for example is an ophthalmology diagnostic equipment, and for example is an image detection device comprises both the tomography device 18 and the fundoscope 14. The diagnostic equipment 2A~2C is used for detecting the eye tissue E. However, the image detection device can merely comprise the tomography device 18 or the fundoscope 14, not limited thereto.

Applying the focusing detection devices 12A~12F in the diagnostic equipment 2C with different embodiments.

FIG. 2A~FIG. 4B illustrate the focusing detection device 12A~12F applying in the illustrate 的 diagnostic equipment 2A~2C of FIG. 5A~FIG. 5C. The focusing detection device 12A~12F applied in the diagnostic equipment 2C are described in detail herein. The focusing detection device 12A~12F can also be applied in diagnostic equipment 2A~2B, details are not repeated herein for simplification.

Figure 6A:
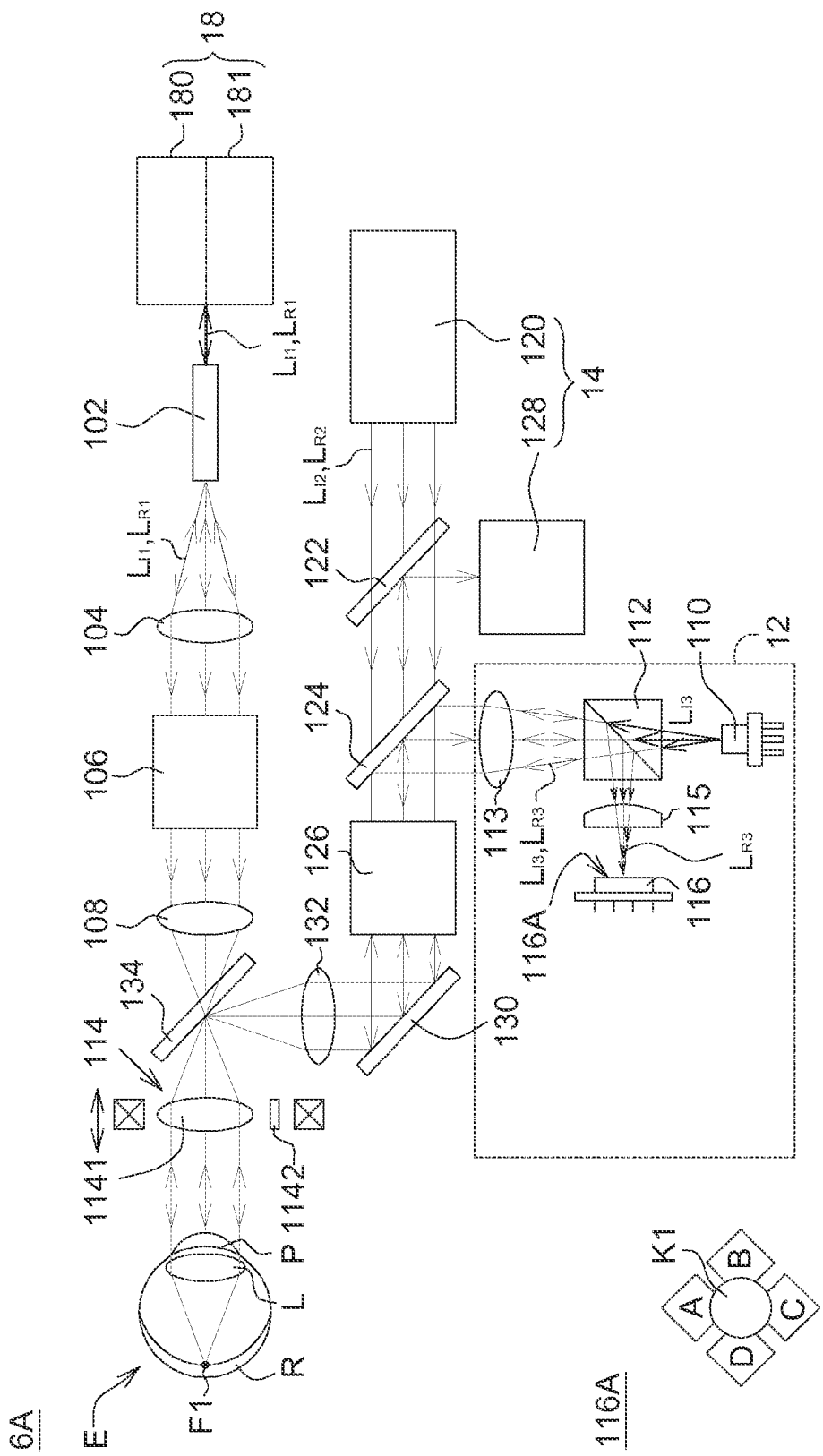
FIG. 6A~FIG. 6C illustrate a focusing detection device in FIG. 2B applied in a diagnostic equipment according to an embodiment of the disclosure.
Figure 6B:
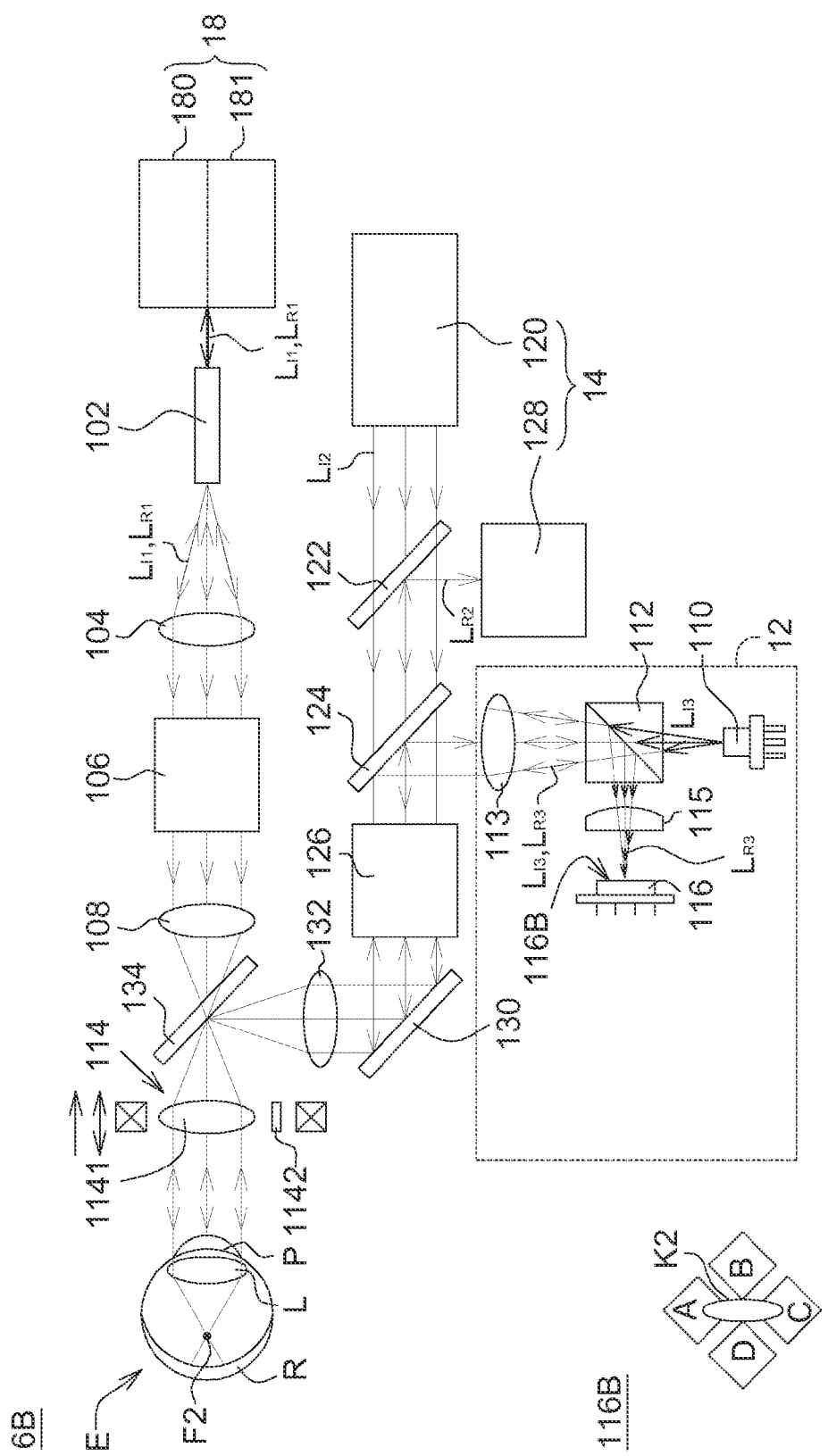
Figure 6C:
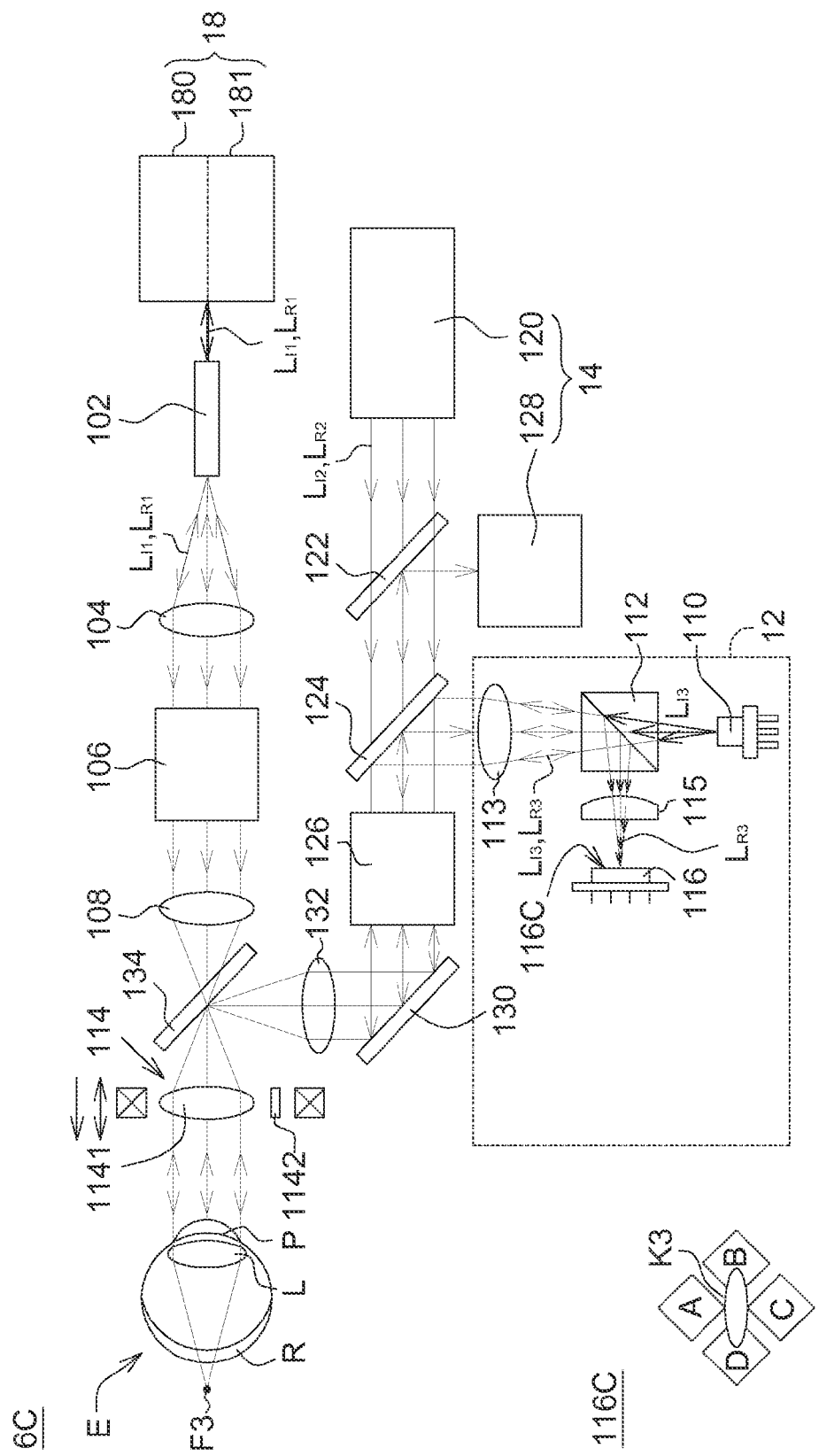

Please refers to FIG. 6A~FIG. 6C. FIG. 6A~FIG. 6C illustrate the focusing positions of the light source of the diagnostic equipment 2C of FIG. 5C according to one embodiment of the disclosure. The focusing positions are on the retina R, in front of the retina R, and in back of the retina R. The fundoscope 14 and the tomography device 18 of FIG. 6A are the same as the fundoscope 14 and tomography device 18 of FIG. 5C. The light source 110 of the focusing detection device 12, the second splitter assembly 112, the second collimating mirror 113, the cylindrical lens 115 and the photo detector 116 are the same as assemblies of the focusing detection device 12B of FIG. 2B, but not limited thereto. In this embodiment, the focusing detection device 12 can also be implemented by ways of the focusing detection device 12A in FIG. 2A.

The fundoscope 14 comprises a light source 120 for providing the light beam $L_{I2}$, an image module 128, a scan assembly 126 and a scan mirror 132. The splitter assembly 124 can be used to integrate the light source 120 of the fundoscope 14 and the light source 110 of the focusing detection device 12. The first splitter assembly 134 is used to integrate the light source 120 of the fundoscope 14, the light source 110 of the focusing detection device 12 and the light source 180 of the tomography. The light beam $L_{I2}$ of the light source 120 in the fundoscope is incident to the eye tissue E and then be reflected to the light beam $L_{R2}$, and transmits to the image module 128. The scan assembly 126 and the scan mirror 132 are shared by the fundoscope 14 and the focusing detection device 12.

After the light beam $L_{I2}$ of the fundoscope light source 120 passing through the splitter assembly 124, the light beam $L_{I2}$ is incident to the scan assembly 126, reflected by the reflecting mirror 130, and passing through the scan mirror 132. Then, the light beam $L_{I2}$ is reflected by the first splitter assembly 134, and passing through the mobile optical lens assembly 114 to reflect the light beam $L_{I2}$ to the pupil P. The eye lens L focuses the substantially parallel light beam $L_{I2}$ at the focusing point F1. The scan assembly 126 can control the path of the light beam $L_{I2}$ to scan the X-Y plane of the focusing position. The light beam $L_{I2}$ focusing on the retina R are reflected by the eye tissue and becomes the light beam $L_{R2}$, the light beam $L_{R2}$ are transmitted along the original path, and reflected by the fifth splitter assembly 122 to the image module 128, the image module 128 converts the signal light to the electrical light to display the scanning image of retina R of the fundus.

Take the tomography device 18 for example, when the light beam $L_{I1}$ is transmitted by the optical fiber 102, and is transmitted through and collimated by the first collimating mirror 104, the collimated light beam $L_{I1}$ passes through the scan assembly 106, the scan mirror 108 and the first splitter assembly 134. The light beam $L_{I1}$ is transmitted through the mobile optical lens assembly 114 to the pupil P, and is focused by the substantially parallel light beam $L_{I1}$ by the eye lens L. The scan assembly 106 can control the path of the light beam $L_{I1}$ to scan the X-Y plane of the focusing position. As shown in FIG. 6A, the light beam $L_{I1}$ focused on the retina R is reflected by the eye tissue and becomes the light beam $L_{R1}$. The light beam $L_{R1}$ incident to the photo detector 181 along the path. The photo detector 181 receives an image signal represented by the light beam $L_{R1}$ for analysis, and analyzes the tomography image of the retina R according to the spectrum of the light beam $L_{R1}$.

As shown in FIG. 6A, the focusing detection device 12 comprises a light source 110, a second splitter assembly 112, a second collimating mirror 113, a cylindrical lens 115, a photo detector 116 and control module (not shown). The focusing detection device 12 is electrical connected to the mobile optical lens assembly 114. The mobile optical lens assembly 114 comprises a lens 1141 and a mobile platform 1142. The mobile platform 1142 for example is an actuator. The control module for example is a processor, a digital processing unit, a microprocessor or a computer. The light beam $L_{I3}$ passes through the second splitter assembly 112 and collimated by the second collimating mirror 113. The collimated light beam $L_{I3}$ is reflected by the fourth splitter assembly 124, and reflected to the scan mirror 132 by the scan assembly 126 and the reflecting mirror 130. Then, the light beam $L_{I3}$ is reflected by the first splitter assembly 134 and passing through the mobile optical lens assembly 114 to transmit the light beam $L_{I3}$ to the pupil P. Then, the substantially parallel light beam $L_{I3}$ is focused at the focusing point F1 by the eye lens L.

In this embodiment, the light beam $L_{I3}$ is reflected by the eye tissue and becomes the light beam $L_{R3}$. After the light beam $L_{R3}$ is incident to the second splitter assembly 112 along the original path, parts of the light is reflected by the cylindrical lens 115 and is split on the photo detector 116. The photo detector 116 of the focusing detection device 12 is the same as the photo detector 116 in FIG. 2A~FIG. 2B. The photo detector 116 is a four quadrant detector with a quadrant A, a quadrant B, a quadrant C and a quadrant D. In FIG. 6A, the distance between the first splitter assembly 134 and the lens 1141 exactly makes the light beam $L_{I3}$ focus at the focusing point F1 on retina R. In this time, the light beam $L_{R3}$ focus on the focusing point K1 of the photo detector 116 on the screen 116A (the surface of the photo detector) along the original path. The energy of the focusing point K1 at a quadrant A plus the energy of the focusing point K1 at a quadrant C, minus the energy of the focusing point K1 at a quadrant B and the energy of the focusing point K1 at a quadrant D is equal to 0. That is to say, the energy received by the quadrant A and the quadrant C is equal to the energy received by the quadrant B and the quadrant D.

Then, the photo detector 116 converts the received signal light into a electrical signal, and then transmits the electrical signal to the control module (not shown) for determination. The control module determines that a distance between the first splitter assembly 134 and the lens 1141 is moderate according to the electrical signal. In this time, a distance between the first splitter assembly 134 and the lens 1141 is moderate so that the light beam $L_{I3}$ can focus at the right position on the retina R. Therefore, the light beam $L_{I1}$ and the light beam $L_{I2}$ can focus on the retina R accurately. The control module (not shown) does not control the movement of the mobile platform 1142.

FIG. 6B illustrates the light source of the diagnostic equipment 6B in FIG. 6B focusing in front of the retina R according to another one embodiment of the disclosure. The components and paths of the light sources of the diagnostic equipment 6B are the same as that of the diagnostic equipment 6A in FIG. 6A. A difference between the diagnostic equipment 6A and the diagnostic equipment 6B is that the focusing positions of the light beams are different. The similarities between the diagnostic equipment 6A and the diagnostic equipment 6B are not described herein. In FIG. 6B, the light beam $L_{I2}$ is focused in front of the focusing point F2 of the retina R, the light beam $L_{I2}$ is reflected by the eye tissue and becomes the light beam $L_{R2}$. The light beam $L_{R2}$ passes along the original path, until the light beam $L_{R2}$ is reflected by the fifth splitter assembly 122 to the image module 128. The image module 128 converts the signal light into an electrical signal to display the scanning image of the fundus. Since the light beam $L_{I2}$ is focused in front of the retina R, the image module 128 can not provide a cleat image of the scanning image of the retina Rs in fundus. Besides, the light beam $L_{I1}$ is focused in front of the retina R, and the photo detector 181 can not analysis the retina R from the tomography according to an optical spectrum of the light beam $L_{R1}$.

In FIG. 6B, a distance between the first splitter assembly 134 and the lens 1141 is too large so that the light beam $L_{R3}$ converges earlier. The light beam $L_{R3}$ is focused on the screen 116B of the photo detector 116 (surface of the photo detector) along the original path, and the focusing point (focusing point) K2 is shown in FIG. 6B. The energy of the focusing point (focusing point) K2 at a quadrant A and a quadrant C minus the energy of the focusing point (focusing point) K2 at a quadrant B and a quadrant D is larger than 0. That is to say, the intensity of light received by a quadrant A and a quadrant C is stronger than the intensity of light received a quadrant B and a quadrant D.

The photo detector 116 then converts the received incident signal light into an electrical signal. The electrical signal is transmitted to the control module (not shown) for determination. The control module determines that a distance between the first splitter assembly 134 and the lens 1141 is too large according to the electrical signal, controls the mobile platform 1142 moving in a direction towards the first splitter assembly 134 according to the electrical signal to reduce the distance between the first splitter assembly 134 and the lens 1141, and adjusts the focusing position of the light beam $L_{I3}$ until the light beam $L_{R3}$ returned from light beam $L_{I3}$ focuses on the screen 116B.

FIG. 6C illustrates the light source focuses in back of the retina R in a diagnostic equipment 6C according to another embodiment the disclosure. As shown in FIG. 6C, the components and the path of light source of the diagnostic equipment 6C are the same as that of the diagnostic equipment 6A in FIG. 6A. Merely the focusing positions of the light beam are different. The similarities between the diagnostic equipment 6C and diagnostic equipment 6A are not described herein. In FIG. 6C, the light beam $L_{I2}$ is focused on the focusing point F3 in back of the retina R, reflected by the eye tissue E and becomes the light beam $L_{R2}$ along the original path to the image module 128. Since the light beam $L_{I2}$ is not focused appropriately on the retina R, the image module 128 can not provide a clear image of retina R in fundus. Similarly, the light beam $L_{I1}$ provided by the light source 180 in the tomography device 18 is focused on the focusing point F3 in back of the retina R. The photo detector 181 can not analysis the retina R by tomography according to light beam $L_{R1}$ optical spectrum, after the light beam $L_{R1}$ incident to the photo detector 181 along the original path.

As shown in FIG. 6C, a light beam $L_{I3}$ provide by the light source 110 of the focusing detection device 12 is focused on the focusing point F3 in back of the retina R. Then, the light beam $L_{I3}$ is reflected by the eye tissue E and becomes the light beam $L_{R3}$. The energy of the light beam $L_{R3}$ focused at the focusing point K3 on the screen 116C (surface of the photo detector) of the photo detector 116 in a quadrant A and a quadrant C, minus the energy of the light beam $L_{R3}$ focused at the focusing point K3 in a quadrant B and a quadrant D is less then 0. That is to say, the light intensity received by the quadrant A and a quadrant C is smaller than the light intensity received by a quadrant B and a quadrant D. The control module (not shown) determines a distance between the first splitter assembly 134 and the lens 1141 is too small according to the electrical signal provided by the photo detector 116, and controls the mobile platform 1142 moving in a direction away from the first splitter assembly 134 according to the electrical signal to increase the distance between the first splitter assembly 134 and the lens 1141 and adjust the focusing position of the light beam $L_{I3}$.

Figure 7A:
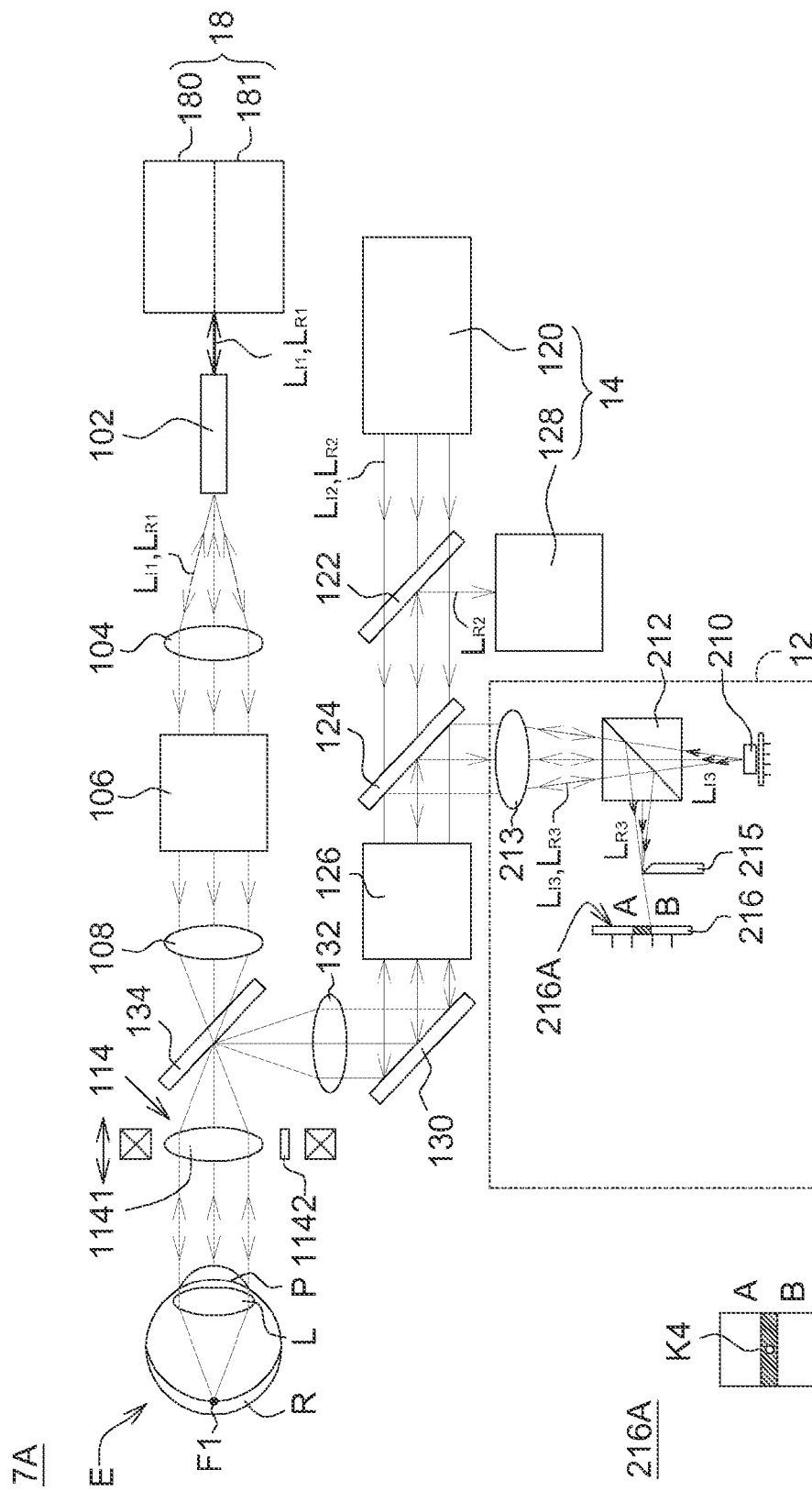
FIG. 7A~FIG. 7C illustrate a focusing detection device in FIG. 3B applied in a diagnostic equipment according to an embodiment of the disclosure.
Figure 7B:
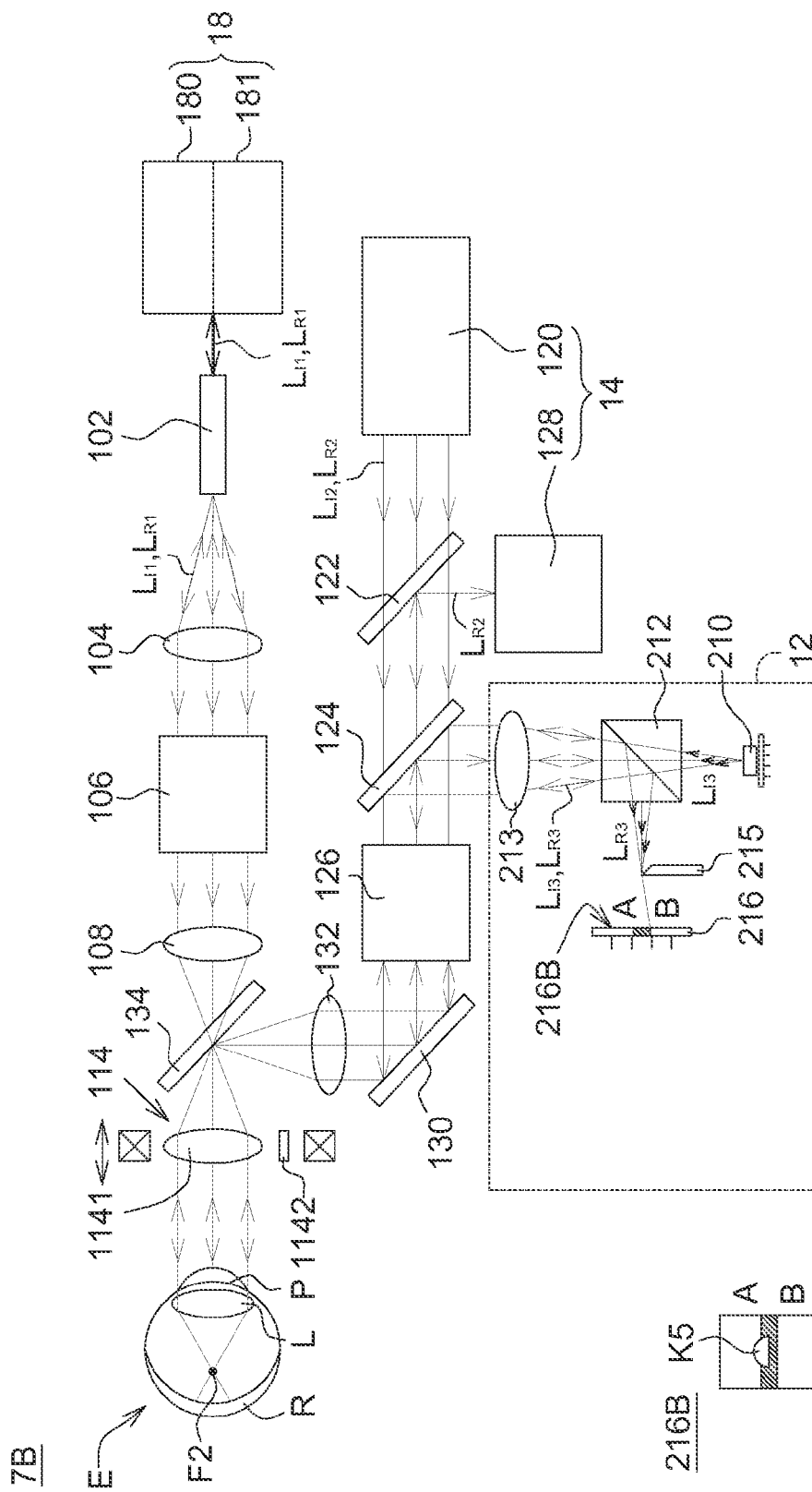
Figure 7C:
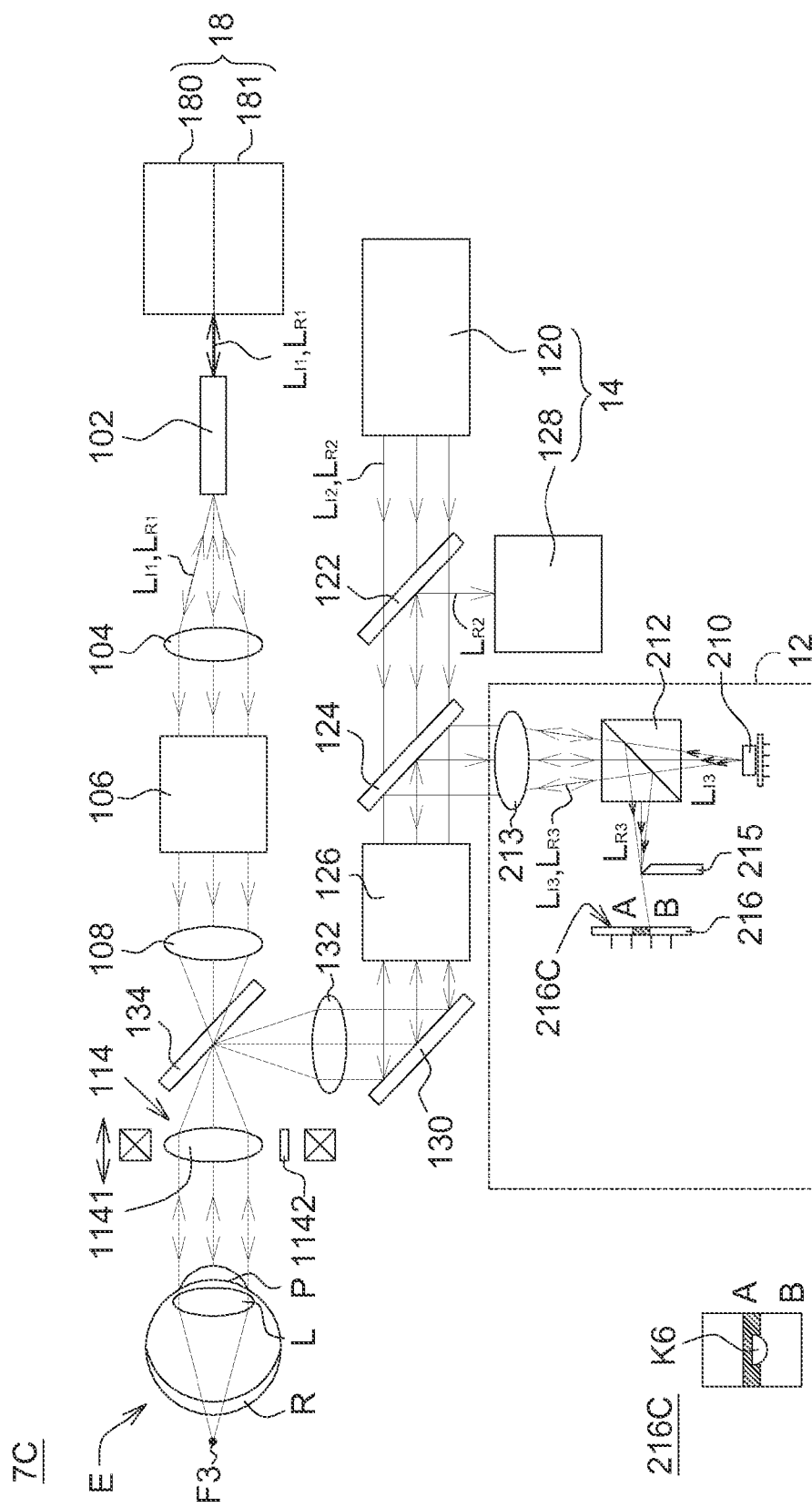

Please refers to FIG. 7A~FIG. 7C. FIG. 7A~FIG. 7C illustrates the light source of the diagnostic equipment 2C in FIG. 5C focused on the retina R, in front of the retina R and in back of the Retina R according to another one embodiment of the disclosure. The tomography device 18 of the diagnostic equipment in this embodiment, the fundoscope 14 and the mobile optical lens assembly 114 are the same as that of the corresponding component in FIG. 6A~FIG. 6C. The components of the focusing detection device 12 in FIG. 7A is the same as the corresponding components of a focusing detection device 12D in FIG. 3B. However, in this embodiment, the focusing detection device 12 can be implemented by ways of the focusing detection device 12C in FIG. 3A, but not limited thereto.

As shown in FIG. 7A, when the light beam $L_{I3}$ passing through the second splitter assembly 212 and collimated by the second collimating mirror 213, the light beam $L_{I3}$ passing through the fourth splitter assembly 124 and is reflected to the scan assembly 126. The light beam $L_{I3}$ is then reflected to the scan mirror 132 by the reflecting mirror 130. Then, the light beam $L_{I3}$ is reflected by the first splitter assembly 134 and passing through the lens 1141 of the mobile optical lens assembly 114 to transmit the light beam $L_{I3}$ to the pupil P. The substantially parallel light beam $L_{I3}$ is focused at the focusing point F1 on the retina R by the eye lens L. Then, the light beam $L_{I3}$ is reflected by the eye tissue E and becomes the light beam $L_{R3}$ along the original path to the second splitter assembly 212. The knife edge of the blade 215 covers a half of the energy of light beam $L_{R3}$, and a residue light beam $L_{R3}$ is focused on the photo detector 216. In FIG. 7A, a distance between the first splitter assembly 134 and the lens 1141 is moderate so that the light beam $L_{I3}$ is focused at the focusing point F1 on the retina R. In this time, the screen 216A (surface of the photo detector) of the photo detector 216 detects a focusing point K4 between a quadrant A and a quadrant B. Therefore, the energy of the focusing point K4 in a quadrant A minus the energy of the focusing point K4 between a quadrant B is equal to 0.

The photo detector 216 converts the received signal light into an electrical signal, and provides the electrical signal to the control module (not shown). The control module determines the distance between the first splitter assembly 134 and lens 1141 is moderate according to the electrical signal, and does not move and control the mobile platform 1142 to adjust the distance between the first splitter assembly 134 and the lens 1141.

Please refers to FIG. 7B. The diagnostic equipment 7B in FIG. 7B is the same as the diagnostic equipment 7A in FIG. 7A, and detail descriptions is not repeated herein. As shown in FIG. 7B, a distance between the first splitter assembly 134 and the lens 1141 is large such that the light beam $L_{I3}$ is focused in front of the focusing point F2 of the retina R. Therefore, the returning light beam $L_{R3}$ converges at an earlier time. In this time, the focusing point K5 detected by the screen 216B (surface of the photo detector) of the photo detector 216 is mainly disposed in quadrant A. The energy of focusing point K5 at a quadrant A minus the energy of the focusing point K5 at a quadrant B is larger than 0.

The photo detector 116 then converts the received signal light into an electrical signal, and provides the electrical signal to the control module (not shown). The control module determines that the distance between the first splitter assembly 134 and lens 1141 is too large according to the electrical signal, and controls the mobile platform 1142 moving in a direction toward the first splitter assembly 134 according to the electrical signal to reduce the distance between the first splitter assembly 134 and the lens 1141 and adjust the focusing position of the light beam $L_{I3}$, until the light beam $L_{R3}$ returns from the light beam $L_{I3}$ is focused on the screen 216B.

The diagnostic equipment 7C in FIG. 7C is the same as the diagnostic equipment in FIG. 7A, the similarities are not described herein. In FIG. 7C, a distance between the first splitter assembly 134 and lens 1141 is small so that the light beam $L_{I3}$ is focused at the focusing point F3 in back of the retina R. The returning light beam $L_{R3}$ is postponed to converge, in this time, the focusing point K6 on the screen 216C (surface of the photo detector) of the photo detector 216 is mainly located at a quadrant B. The energy of focusing point K6 at the quadrant A minus the energy of focusing point K6 at a quadrant B is smaller than 0. Then, the control module (not shown) determines that the distance between the first splitter assembly 134 and the lens 1141 is too small according to the electrical signal provided by the photo detector 216. The control module controls the mobile platform 1142 moving away from the first splitter assembly 134 according to the electrical signal to increase the distance between the first splitter assembly 134 and the lens 1141 and adjust the focusing position of the light beam $L_{I3}$, until the returning light beam $L_{R3}$ from the light beam $L_{I3}$ is focused on the screen 216C.

Figure 8A:
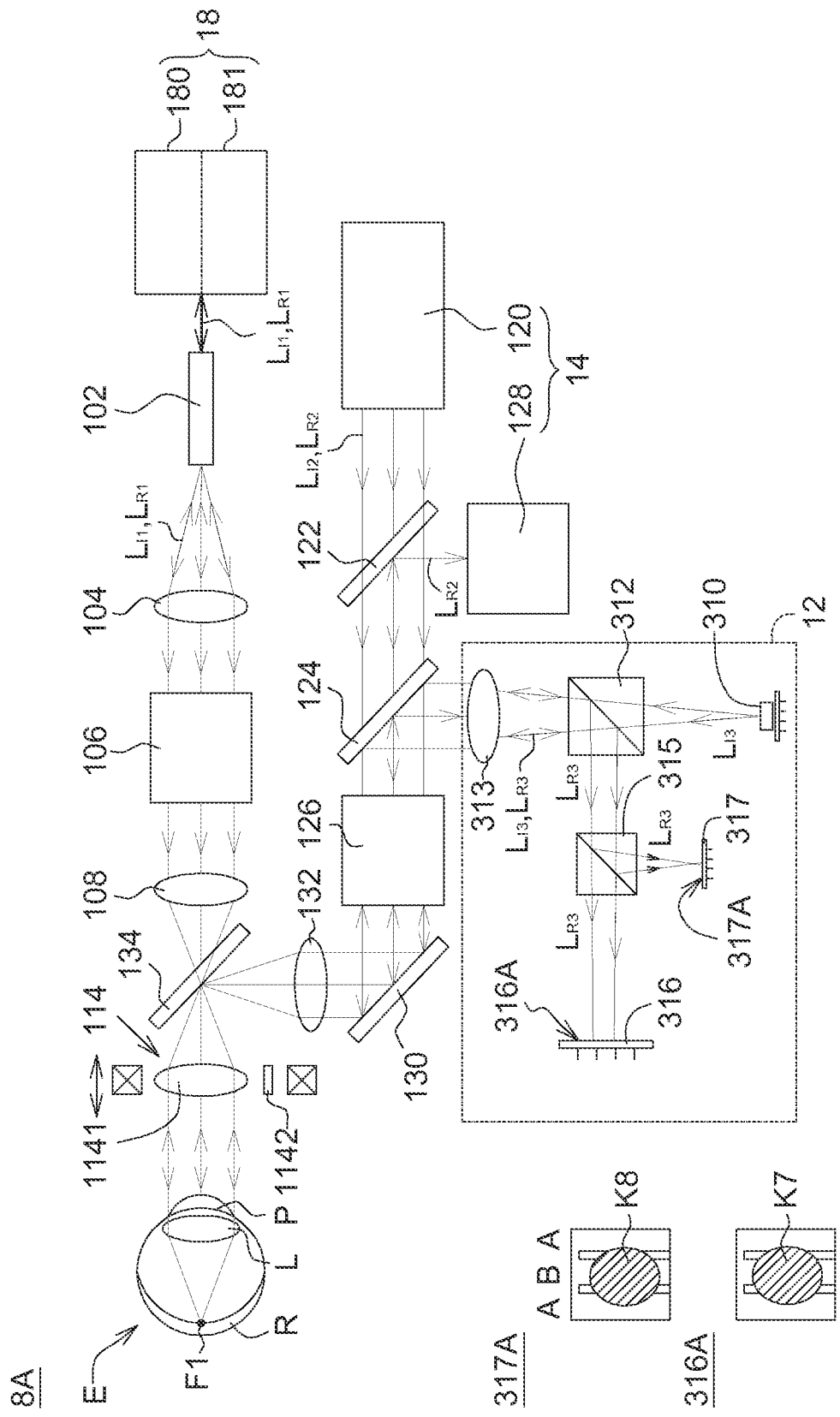
FIG. 8A~FIG. 8C illustrate a focusing detection device in FIG. 4B applied in a diagnostic equipment according to an embodiment of the disclosure.
Figure 8B:
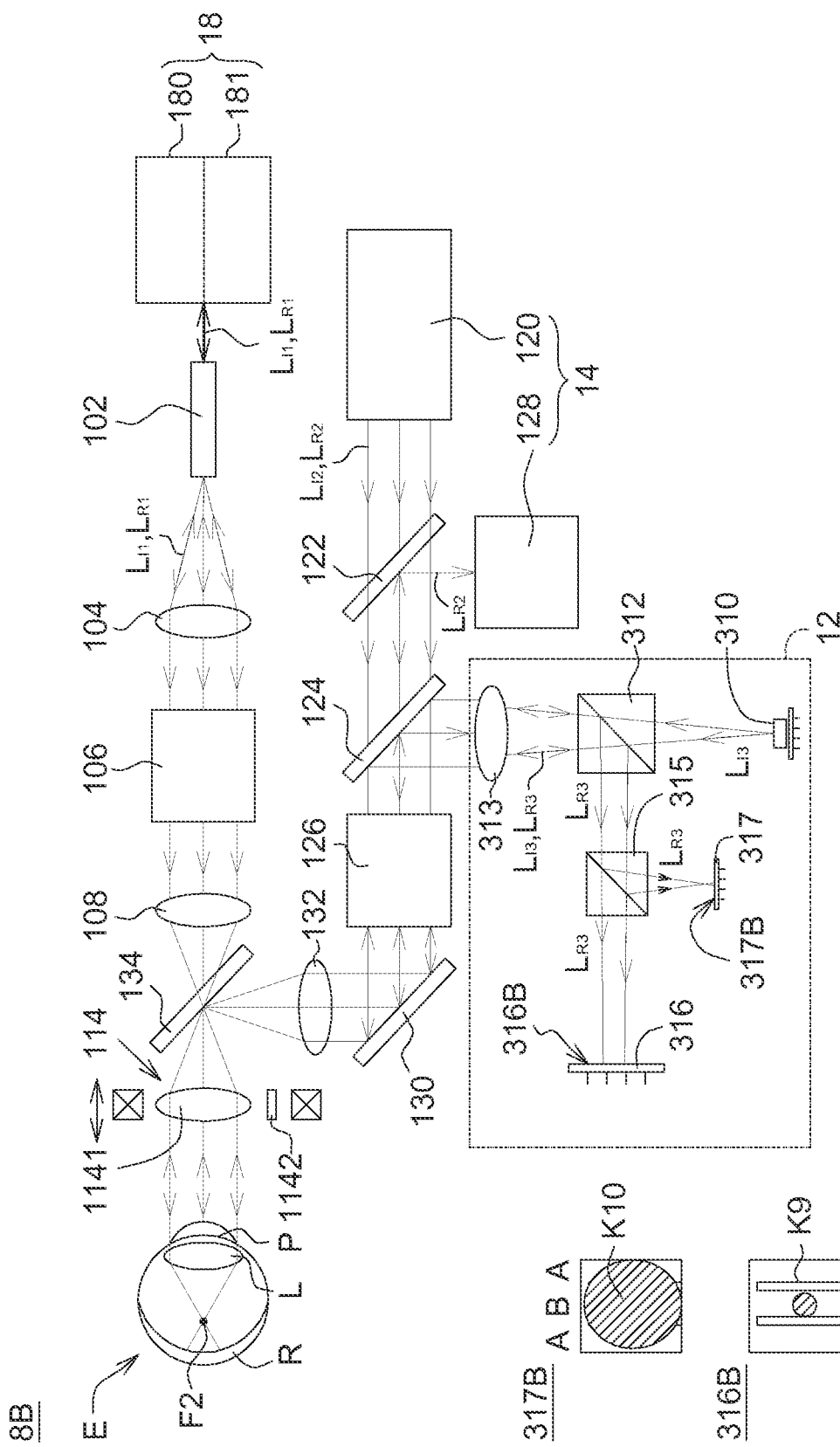
Figure 8C:
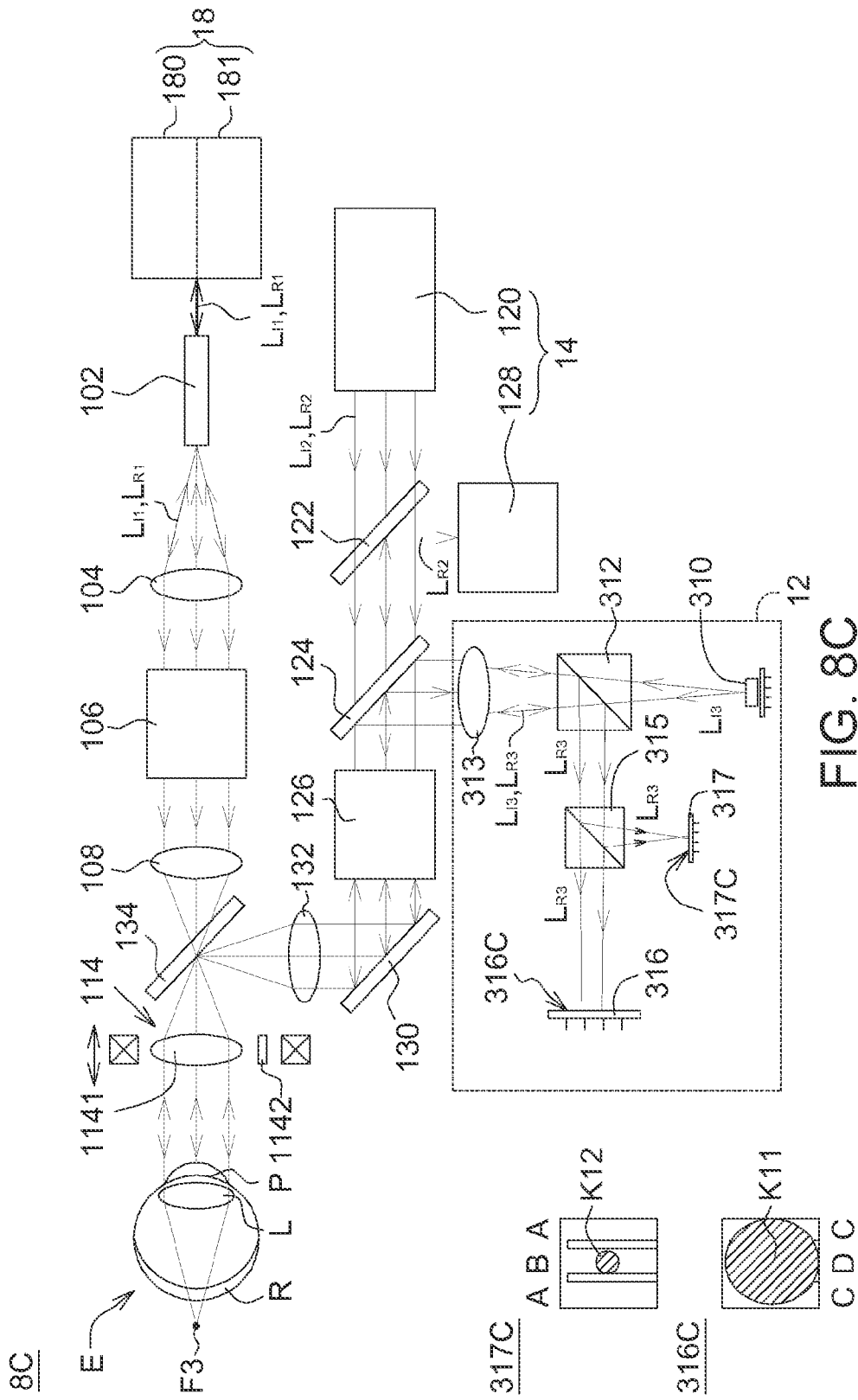

Please refers to FIG. 8A~FIG. 8C. FIG. 8A~FIG. 8C illustrates another embodiment of the diagnostic equipment 2C in FIG. 5C focused on the retina R, in front of the retina R and in back of the retina R. In this embodiment, the tomography device 18 and the fundoscope 14 of the diagnostic equipment and the mobile optical lens assembly 114 are the same as that of the corresponding components in FIG. 6A~FIG. 6C and in FIG. 7A~FIG. 7C and are not described repeatedly herein. It is noted that the focusing detection device 12 in FIG. 8A is the same as the corresponding focusing detection device 12F of FIG. 4B. However, the focusing detection device 12 can also be used by ways of the focusing detection device 12E of FIG. 4A in this embodiment, and not limited thereto. The photo detector 316 and photo detector 317 for example are a quadrant detectors. The three quadrant of the photo detector 316 are respectively a quadrant C, a quadrant D and a quadrant C, and three quadrant of the photo detector 317 are a quadrant A, a quadrant B and a quadrant A.

Please refers to FIG. 8A, the light source 310 of the focusing detection device 12 can provide a light beam $L_{I3}$. After the light beam $L_{I3}$ passing through the second splitter assembly 312, the light beam $L_{I3}$ collimated through the collimating mirror 313 and reflected by the fourth splitter assembly 124, and passing through the scan assembly 126 to the reflecting mirror 130, and reflected by the reflecting mirror 130 to the scan mirror 132. Then, light beam $L_{I3}$ is reflected by the first splitter assembly 134 and passes through the lens 1141 of the mobile optical lens assembly 114 so that the light beam $L_{I3}$ is transmitted to the pupil P. The substantially parallel light beam $L_{I3}$ is focused by the eye lens L on the focusing point F1 of the retina R, the light beam $L_{I3}$ is then reflected by the eye tissue E and becomes the light beam $L_{R3}$.

As shown in FIG. 8A, the returning light beam $L_{R3}$ passing through the second splitter assembly 312 is reflected to the third splitter assembly 315 and passing through the third splitter assembly 315, and is transmitted to the photo detector 317 and photo detector 316. When a distance between the first splitter assembly 134 and lens 1141 makes that the light beam $L_{I3}$ is focused at the focusing point F1 on the Retina R, the focusing point K8 on the screen 317A (surface of photo detector) of the photo detector 317 is in back of the focal point of the second collimating mirror, if the energy of the focusing point K8 at a quadrant A minus the energy of the focusing point K8 at a quadrant B is equal to P1. The focusing point K7 focused on the screen 316A (surface of photo detector) of the photo detector 316 is in front of the focal point of the second collimating mirror, if the energy of the focusing point K7 at a quadrant C minus the energy of the focusing point K7 at a quadrant D is equal to P2, and P1−P2=0. The photo detector 316 and photo detector 317 then converts the incident signal light into an electrical signal and then provides the electrical signal to the control module (not shown). The control module determines that the distance between the first splitter assembly 134 and the lens 1141 is moderate and does not move the mobile platform 1142 according to the electrical signal.

Please refers to FIG. 8B, a light path of the light beam $L_{I3}$ is similar to that in FIG. 8A, the similarities are not described herein. It is noted that the distance between the first splitter assembly 134 and lens 1141 in FIG. 8B is larger than that in FIG. 8B. The light beam $L_{I3}$ focused at the focusing point F2 in front of the Retina R, and the returning light beam $L_{R3}$ converge earlier. In this time, the focusing point K10 on the screen 317B (surface of photo detector) of the photo detector 317 is far away from and getting larger than focusing. The energy of focusing point K10 at a quadrant A minus the energy of focusing point K10 at a quadrant B is larger than P1 in the embodiment of FIG. 8A. The focusing point K9 on the screen 316B (surface of photo detector) of the photo detector 316 is close to focus and getting smaller, and the energy of the focusing point K9 at a quadrant C minus the energy of the focusing point K9 at a quadrant D is smaller than P2 described in the embodiment of FIG. 8A, and P1−P2>0. The photo detector 316 and photo detector 317 then convert the incident signal light into an electrical signal and provide the electrical signal to the control module (not shown), the control module determines that the distance between the first splitter assembly 134 and lens 1141 is too large. The control module controls the mobile platform 1142 moving in a direction towards the first splitter assembly 134 according to the electrical signal to reduce the distance between the first splitter assembly 134 and lens 1141 and adjust the focusing position of the light beam $L_{f3}$, until the light beam $L_{f3}$ focuses on the screen 316B and the screen 317B accurately.

Please refers to FIG. 8C, the light path of the light beam $L_{f3}$ is the same as the light path of the light beam $L_{f3}$ in FIG. 8A, the similarities are not repeated herein. It is noted that a distance between the first splitter assembly 134 and the lens 1141 is smaller in FIG. 8C than that in FIG. 8A. The light beam $L_{f3}$ focused at the focusing point F3 in back of the retina R. The returning light beam $L_{R3}$ postpone to converge. In this time, the focusing point K12 on the screen 317C (surface of photo detector) of photo detector 317 is about to focus and getting smaller, and the energy of the focusing point K12 at a quadrant A minus the energy of the focusing point K12 at a quadrant B is smaller than P1 described in the embodiment of FIG. 8A. The focusing point K11 on the screen 316C (surface of photo detector) of the photo detector 316 is away from being focused and getting larger, and the energy of the focusing point K11 at a quadrant C of screen 316C minus the energy of the focusing point K11 at a quadrant D is energy P2. The value of P2 in FIG. 8C is larger than the value of P2 in the embodiment of FIG. 8A, so that P1−P2<0. The control module (not shown) determines the distance between the first splitter assembly 134 and lens 1141 is too small according to the electrical signal provided by the photo detector 316. The control module controls the mobile platform 1142 moving in a direction away from the first splitter assembly 134 to increase the distance between the first splitter assembly 134 and the lens 1141 to adjust the focusing position of the light beam $L_{f3}$, until the light beam $L_{f3}$ can focus on the screen 316C and the screen 317C appropriately.

Figure 9:
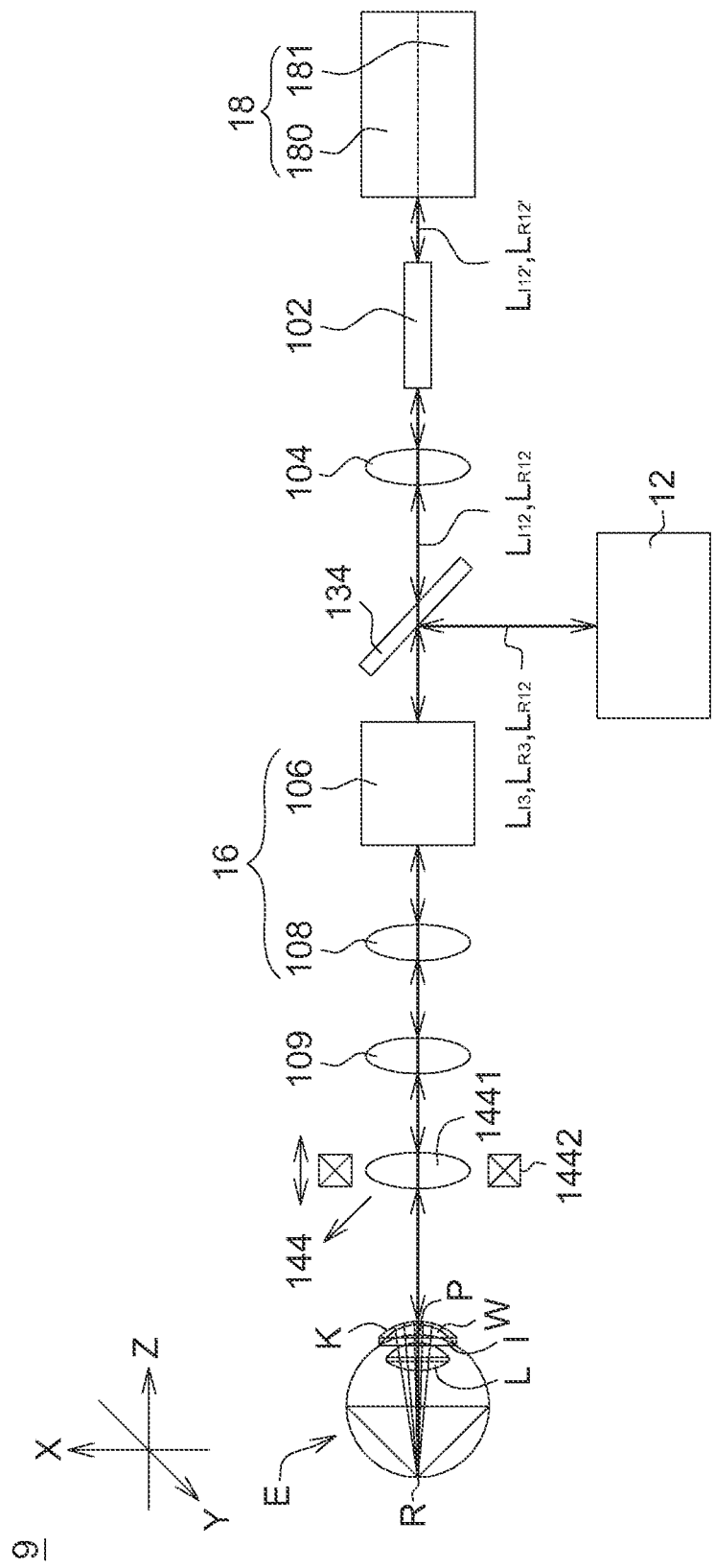
FIG. 9 illustrates a diagnostic equipment according to another one embodiment of the disclosure.

FIG. 9 illustrates the diagnostic equipment 9 according to another one embodiment of the disclosure. As shown in FIG. 9, the diagnostic equipment 9 comprises a tomography device 18, an optical fiber 102, a first collimating mirror 104, a first splitter assembly 134, a focusing detection device 12, a scan device 16, an ocular lens 109 and a mobile optical lens assembly 144. The diagnostic equipment 9 in FIG. 9 and the diagnostic equipment 1B in FIG. 1B are similar to each other, difference between the diagnostic equipment 9 and the diagnostic equipment 1B is that the diagnostic equipment 9 further comprises the ocular lens 109. The diagnostic equipment 9 is mainly used for detecting the cornea K, the anterior chamber W or the eye lens L of the eye tissue E.

The optical fiber 102 can be disposed selectively, the first splitter assembly 134 for example is a beam splitter, a splitting diffraction assembly, a splitter optical fiber assembly or a splitter waveguide assembly. The scan device 16 comprises a scan mirror 108 and a scan assembly 106. The scan assembly 106 for example is a pair of galvano-meter scanning reflecting mirror. The tomography device 18 can comprise a tomography light source 180 and a photo detector 181. The mobile optical lens assembly 144 comprises a focusing lens 1441 and a mobile platform 1442.

In this embodiment, the light source 180 for example is an uncollimated near-infrared light source used for providing a light beam $L_{f12}$. The focusing detection device 12 is electrical connected to the mobile optical lens assembly 144. The photo detector 181 for example is a charge coupling diode (CCD), a CMOS, a PIN (Positive Intrinsic Negative) detector or an avalanche photo detector. In other embodiments, light sources with other waveform ranges can be selected as the light source 180 according to the requirement. The light source is not limited to the light source with waveforms within a near-infrared.

In embodiment of FIG. 9, when the light beam $L_{f12}$ passing through the first splitter assembly 134, the scan device 16 and the ocular lens 109, the light beam $L_{f12}$ remains a parallel light beam until it incident to the mobile optical lens assembly 144. The focusing lens 1441 can focus the original parallel light beam $L_{f12}$, and controls the mobile platform 1442 that carries the focusing lens 1441 along the optical axis to make the light beam $L_{f12}$ focus on the cornea K, the anterior chamber W or the eye lens L of the eye tissue E, such that the light beam $L_{f12}$ becomes a light beam $L_{R12}$. The scan device 16 is used for making the light beam incident to the eye tissue E scans along the X-Y plane of the specific tissue (such as the cornea K, the anterior chamber W or the eye lens L). The refraction coefficient of the light beam $L_{R12}$ focused on the interface between the tissues is significant, especially to the interface between the cornea and the air. Therefore, the intensity of signal received from the light beam focused on the interface between the tissues is stronger.

As shown in FIG. 9, the first splitter assembly 134 is used for splitting the light beam $L_{R12}$ into two light paths to the photo detector 181 and the focusing detection device 12, respectively. If the first splitter assembly 134 is a beam splitter, the described beam splitter for example is a partially light-transmittable and partially light-reflectable beam splitter. The focusing detection device 12 receives a signal light of the light beam $L_{R12}$, and controls the movement of the mobile platform 1142 according to the detected signal to adjust the focusing position of the light beam $L_{f12}$.

Figure 10:
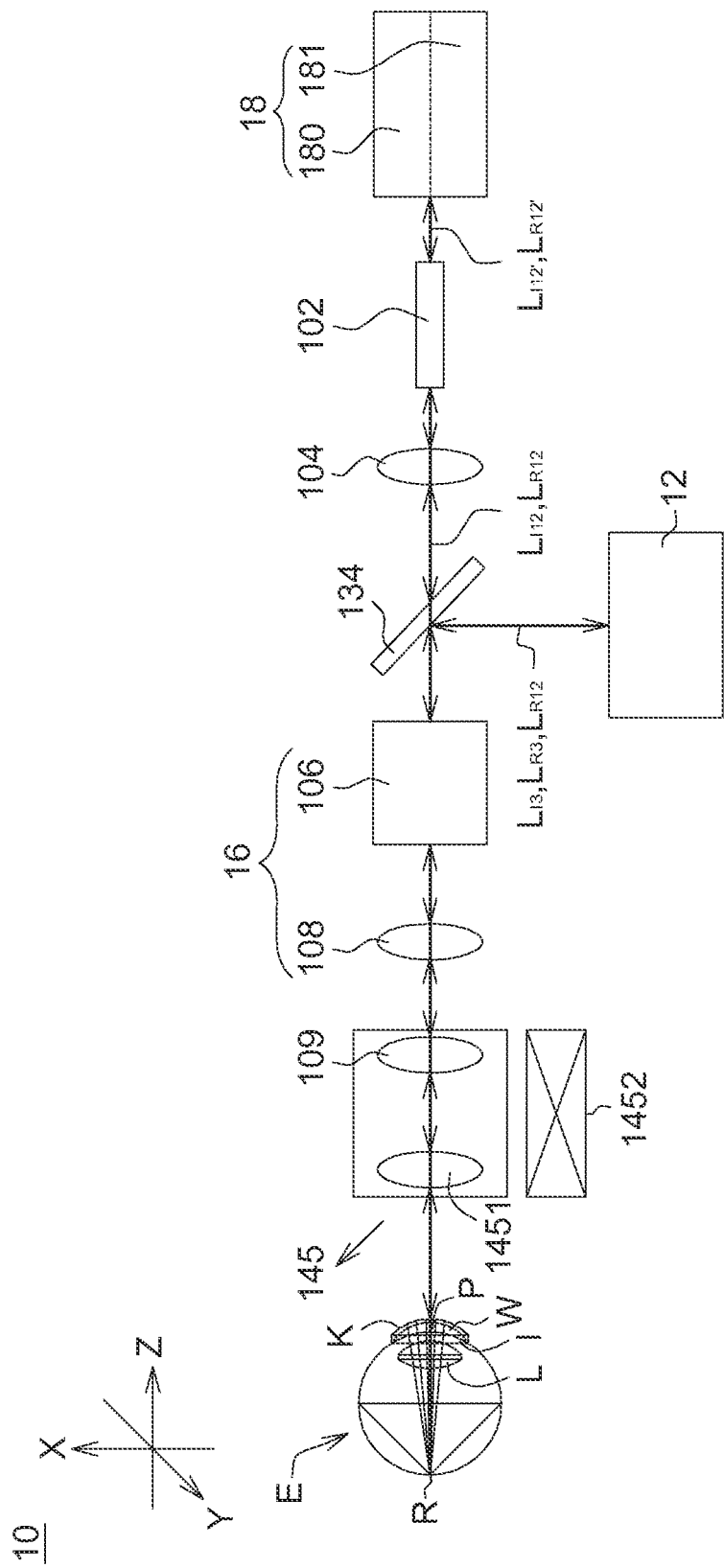
FIG. 10 illustrates a diagnostic equipment according to one embodiment of the disclosure.

FIG. 10 illustrates the diagnostic equipment 10 according to an embodiment of the disclosure. As shown in FIG. 10, the diagnostic equipment 10 is similar to the diagnostic equipment 9 in FIG. 9, the similarities are not described and repeatedly herein. The difference between the diagnostic equipment 10 and the diagnostic equipment 9 is that the mobile optical lens assembly 145 comprises a focusing lens 1451, a mobile platform 1452 and an ocular lens 109 in FIG. 9. The focusing detection device 12 is electrical connected to the mobile optical lens assembly 145. When adjusting the focusing position of the light beam $L_{f12}$, the focusing lens 1451 and the ocular lens 109 are controlled by the mobile platform 1452 simultaneously.

Figure 11:
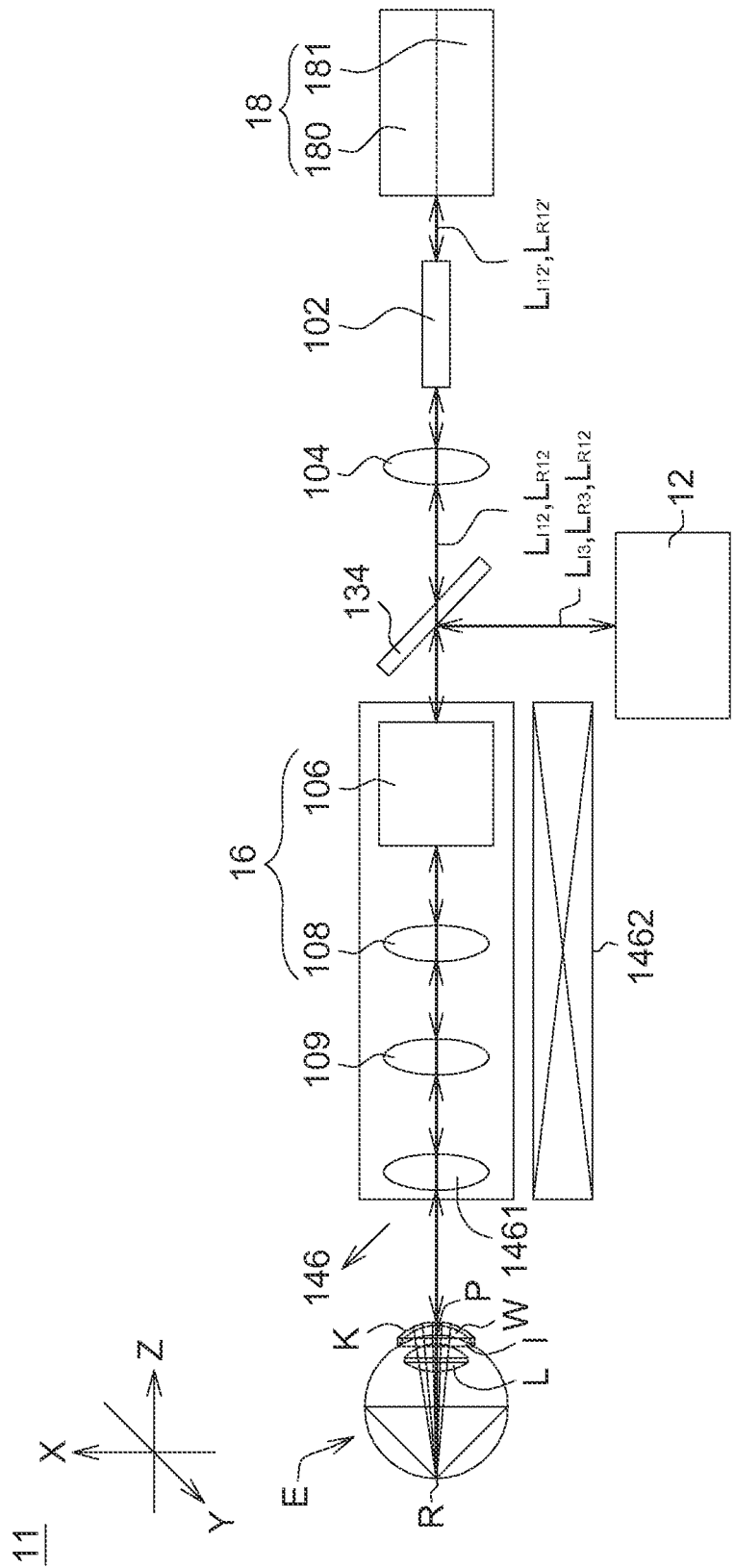
FIG. 11 illustrates a diagnostic equipment according to one embodiment of the disclosure.

FIG. 11 illustrates the diagnostic equipment 11 according to an embodiment of the disclosure. As shown in FIG. 11, the diagnostic equipment 11 is similar to the diagnostic equipment 9 in FIG. 9, the similarities are not repeatedly herein. The difference between the diagnostic equipment 11 and the diagnostic equipment 9 is that the mobile optical lens assembly 146 comprises a scan device 16, a focusing lens 1461, a mobile platform 1462 and an ocular lens 109. Therefore, the focusing detection device 12 is electrical connected to the mobile optical lens assembly 146. When adjusting the focusing position of the light beam $L_{f12}$, the scan device 16, the ocular lens 109 and the focusing lens 1461 are controlled by the mobile platform 1462 simultaneously.

In one embodiment, the mobile platform 1462 of the mobile optical lens assembly 146 can be designed to carry and move with more components. For example, the mobile platform 1462 can further carry and move with the first splitter assembly 134 and the focusing detection device 12, or carry and move with the first splitter assembly 134, the focusing detection device 12, the first collimating mirror 104 and the optical fiber 102a.

In this embodiment, a distance between the anterior chamber mirror, the ocular lens and the scan mirror with respect to the relative position of the patient remain the same during the auto-focusing process. Therefore, the light emitting condition of the scan mirror remains the same, and the scale bar would not be changed. In this case, the system can be applied to measure the size of the eyeball or the size of the affected part. For example, assuming a relationship between the focusing lens 1461 and the ocular lens 109 is telecentric during the tomography scan of the anterior chamber. That is to say, the optical axis of any emitting light beam emitted from the focusing lens 1441, focusing lens 1451 or focusing lens 1461 is parallel to the central axis or the optical axis of the device. Therefore, the scale bar of the final image remains the same. Therefore, the mobile optical lens assembly 146 controls the focusing lens 1461, the ocular lens 109 and the scan device 16 moving back and forth simultaneously. The relative position of the components, the scale of the scan image can remain the same.

Figure 12:
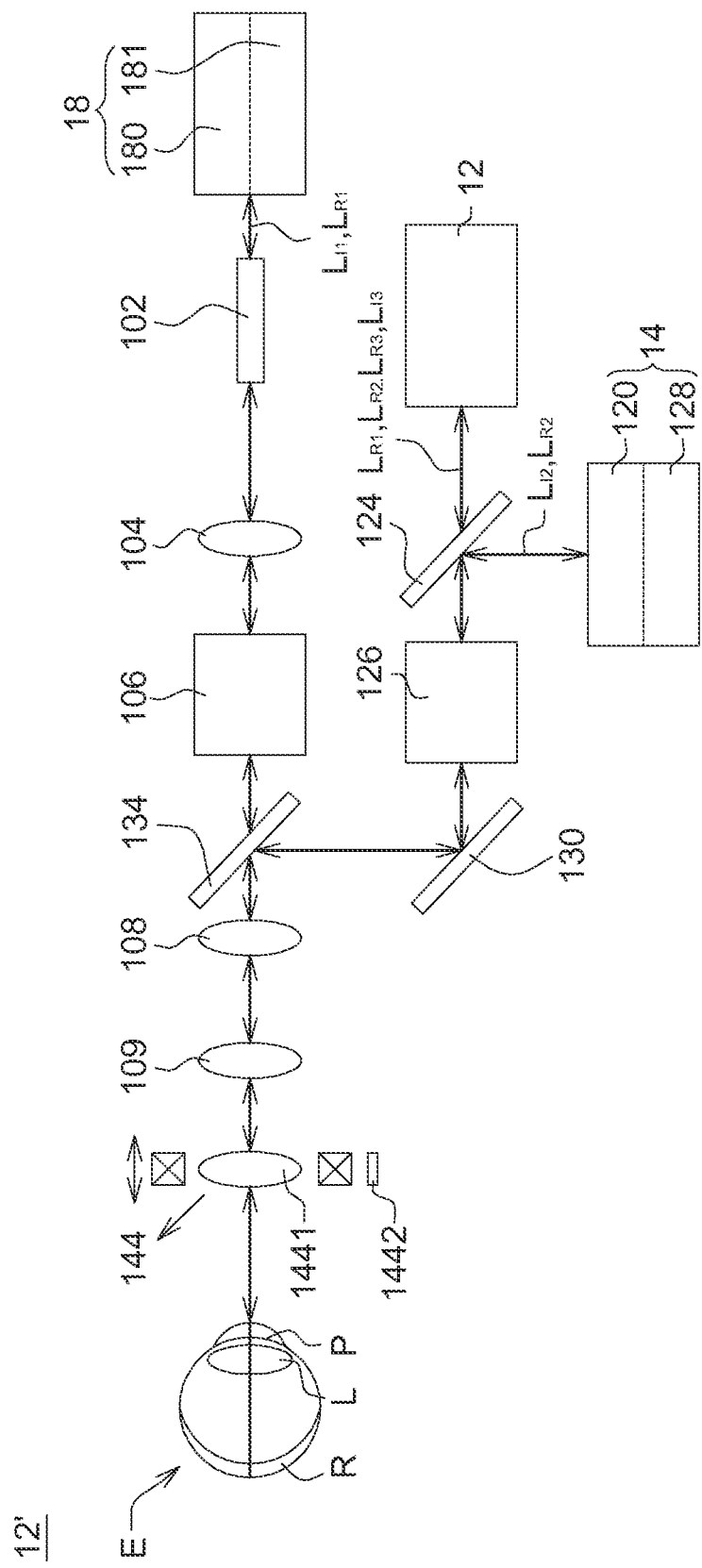
FIG. 12 illustrates structural features of a diagnostic equipment in FIG. 9 according to one embodiment of the disclosure.

FIG. 12 illustrates a detail description of the diagnostic equipment 9 in FIG. 9 according to the disclosure. As shown in FIG. 12, the diagnostic equipment 12' comprises a tomography device 18, a focusing detection device 12 and a fundoscope 14. The tomography device 18 comprises a tomography light source 180 and a photo detector 181. The diagnostic equipment 12' is similar to the diagnostic equipment 2A in FIG. 5A, the similarities are not repeatedly herein. The differences between the diagnostic equipment 12' and the diagnostic equipment 2A is that the diagnostic equipment 12' further comprises an ocular lens 109. The focusing lens 1141 is controlled by the mobile platform 1142 and the position of the focusing lens 1141 can be adjusted. Therefore, the diagnostic equipment 12' can be applied in fundus detection as well as detection to the cornea K, anterior chamber W or eye lens L of the eye tissue E.

The optical imitation image of the experiment results of the diagnostic equipment 6A in FIG. 6A is imitated and constructed by Zemax software.

In order to reduce the complexity of the imitation, the diagnostic equipment 6A of FIG. 6A is simplified herein. The simplification hardly affects the final results. Details are described as follows. Please refer to FIG. 6A, an emitting light path of the auto-focusing detect module 12 comprises a laser light source 110, a beam splitter 112 and a collimating mirror 113. The returning light path of the auto-focusing detect module 12 comprises a collimating mirror 113 (used as a focusing lens), a beam splitter 112, a cylindrical lens 115 and a quad-division photo detector 116.

When the laser light beam $L_{f3}$ and the light beam $L_{R3}$ are emitted from the collimating mirror 113 and collimated by a collimating mirror 113g, the laser light beam $L_{f3}$ becomes a parallel light that reflected by the fourth splitter assembly 124 (such as a reflecting mirror) and then transmitted to the scan assembly 126. The laser light beam $L_{f3}$ is then incident to the reflecting mirror 130, reflected by the reflecting mirror 130 and then incident to the scan mirror 132 to be focused. The focused light beam is transmitted to the first splitter assembly 134 and reflected by the first splitter assembly 134, and then transmitted to the lens 1141 and finally enters the eye tissue E.

In this embodiment, the laser light beam used in the focusing detection device 12 passes through three reflecting mirrors in front of the eye tissue E. The three reflecting mirrors are the fourth splitter assembly 124, the reflecting mirror 130 and the first splitter assembly 134, which are used for changing the path of the laser light beam, but not the convergence or the divergence of the laser light beam. Therefore, the reflecting mirrors can be omitted without affecting the path of the laser light beam that enters the eye tissue E in the imitation experiments.

Figure 13:
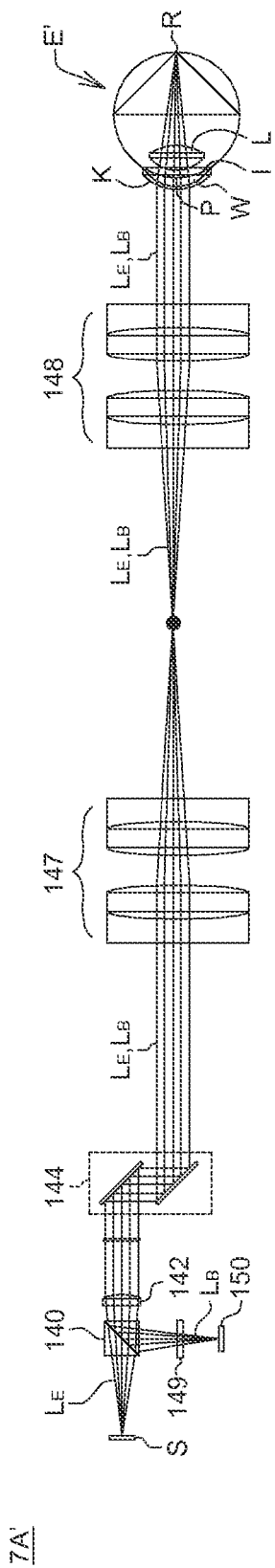
FIG. 13 illustrates a diagnostic equipment in FIG. 6A omitting parts of components constructed by Zemax imitate software.

FIG. 13 illustrates a diagnostic equipment 7A' constructed by Zemax software intimation when omitting the fourth splitter assembly 124, the reflecting mirror 130 and the first splitter assembly 134 in the diagnostic equipment 6A of FIG. 6A. As shown in FIG. 13, after the light source S providing a laser light beam $L_E$ with a wavelength of 780 nm is emitted and passes through a distance of 14.15 mm, the laser light beam $L_E$ is transmitted to the 6 mm splitter prism 140 (with a BK7 material). Then, the laser light beam $L_E$ is transmitted along a 3 mm distance and is incident to a plastic non-spherical collimating mirror 142 with an outer diameter of 6.6 mm. In this time, the light beam $L_E$ becomes a parallel light beam transmitting through a distance of 20 mm. The light beam $L_E$ is then transmitted to the scan mirror assembly 144 (typically are reflecting mirrors of more than two galvanometers). The scan mirror assembly 144 can comprise a motor or micro motor (not shown), for controlling the reflective angles of the mirror and adjust a direction of the path of the parallel light beam. In this embodiment, a distance between the centers of the two reflecting mirrors in the scan mirror assembly 144 is 9.7 mm. If mirrors of the scan mirror assembly 144 are located at a center position, the laser light beam $L_E$ is reflected by the two reflecting mirrors of the scan mirror assembly 144 and is transmitted to a center of the scan mirror 147.

In this imitation, a pair of mirror aplanat assembly is used as the scan mirror 147. The mirror parameters such as the radius of curvature of the mirror aplanat assembly from the incident direction of the light beam to the emitting direction of the light beam, are 656.51 mm, 57.01 mm, −57.01 mm, 57.01 mm, −57.01 mm and −656.51 mm. The thicknesses of the mirror aplanat assembly from the incident direction of the light beam to the emitting direction of the light beam, are 4 mm, 6 mm, 5.45 mm, 6 mm and 4 mm. The materials of the mirror aplanat assembly from the incident direction of the light beam to the emitting direction of the light beam, are SFL6, LAKN22, air, LAKN22, SFL6. The laser light beam $L_E$ emitting from the scan mirror 147 is focused at a distance of 42.54 mm far from the scan mirror assembly 144. Then, the focused laser light beam $L_E$ diverges and passes through a distance of 19.23 mm to be transmitted to the ocular lens 148.

In this imitate, another one pair of mirror aplanat assembly is used as the ocular lens 148. The mirror parameters such as the radius of curvature of another one mirror aplanat assembly from the incident direction of the light beam to the emitting direction of the light beam, are 392.21 mm, 42.9 mm, −43.96 mm, 31.69 mm, −28.45 mm and −161.05 mm. The thicknesses of the another one pair of the mirror aplanat assembly are 4 mm, 6 mm, 3.97 mm, 8 mm and 4 mm. The materials of the another one pair of the mirror aplanat assembly are SFL6, LAKN22, air, LAKN22 and SFL6. The laser light beam $L_E$ emits from the ocular lens 148 and passes through air with a distance of 20.08 mm to be transmitted to the cornea K of the eye tissue E'.

In this imitation, the eyeball model provided by the website of radiant zemax is used as the eye tissue E'. The diameter of the eyeball model is 24 mm. The thickness of the cornea is 0.52 mm. The thickness of the anterior chamber W is 2.7 mm. The thickness of the iris I is 0.1 mm. The thickness of the eye lens L is 4.3 mm. After the laser light beam $L_E$ incident to the cornea K of the eye tissue E', the laser light beam $L_E$ passes through a distance of 16.38 mm to a surface of the retina R. The imitation parameters are provided by Radiant Zemax Company. For example, the material of the cornea is Cornea (n=1.38), the materials of the aqueous fluid and the iris are Aqueous (n=1.34). The material of the eye lens is Lens (n=1.42), and the material of the inner side of the eyeball is Aqueous (n=1.34). The laser light beam $L_E$ is focused on a surface of the retina R by the cornea K and eye lens L. If the surface of the retina R is smooth and the reflectivity of the surface is higher than that of the adjacent tissue, most of the laser light beam $L_E$ are reflected by the retina R. Merely partial of the laser light beam $L_E$ can penetrate the retina R first and then reflected by the retina R. The intensity of the penetration is highest on the surface of the retina R.

The laser light beam $L_B$ reflected by a surface of the retina R and passing through the pupil P can return back along the original path. That is to say, the laser light beam $L_B$ passes through the ocular lens 148, the scan mirror 147, the scan mirror assembly 144 respectively and then is transmitted to the collimating mirror 142. Then, the laser light beam $L_B$ is transmitted to the 6 mm beam splitter prism 140. In this time, part of the light beam $L_B$ can be reflected by the beam splitter prism 140 and then is incident to the cylindrical lens 149. The distance between the cylindrical lens 149 and the beam splitter prism 140 is substantially 8 mm. Then, the light beam $L_B$ passes through a distance of 5.72 mm to be incident to the quad-division photo detector 150. In this imitation, the radius of curvature of the cylindrical lens 149 is 25 mm, the thickness of the cylindrical lens 149 is 1 mm, and the material of the cylindrical lens 149 is BK7. The length of the photo detector 150 is 123 μm, and a distance between the adjacent division is 5 μm.

Figure 14A:
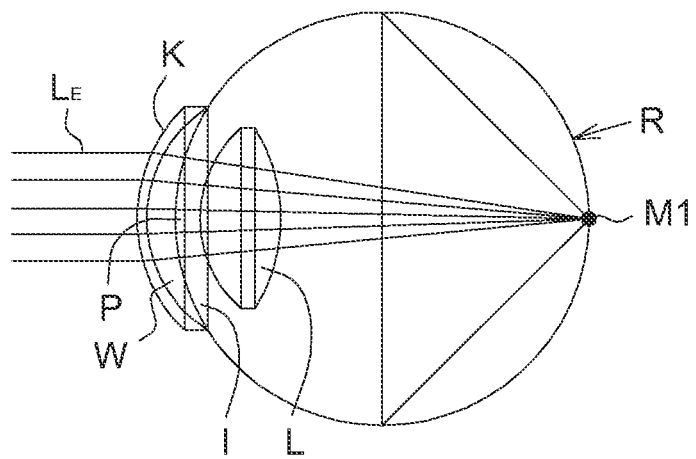
FIG. 14A illustrates an optical path of a light beam imitated according to a diagnostic equipment in FIG. 13 applied in an ordinary eye tissue.
Figure 14B:
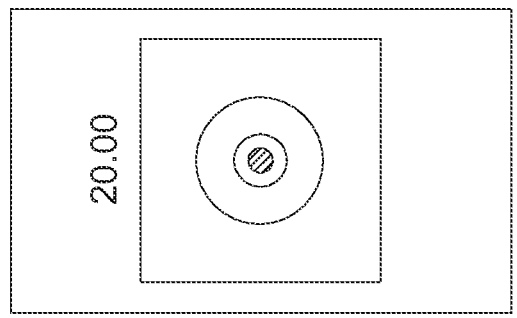
FIG. 14B illustrate a result of a focusing point on the retina in FIG. 14A.

FIG. 14A illustrates an imitation of the optical path of the light beam $L_E$ in the diagnostic equipment 7A' in FIG. 13 applying in the ordinary eye tissue E1 according to one embodiment of the disclosure. As shown in FIG. 14A, the light beam $L_E$ can focus on the retina R accurately. FIG. 14B illustrates the focusing point M1 on the retina R in FIG. 14A. The software of Zemax analyzes the imitating result according to FIG. 14B. The focusing point M1 and the radius of the root mean square (RMS) is 1.58 μm. The radius of the luminescent spot is 5.2 μm.

Figure 15A:
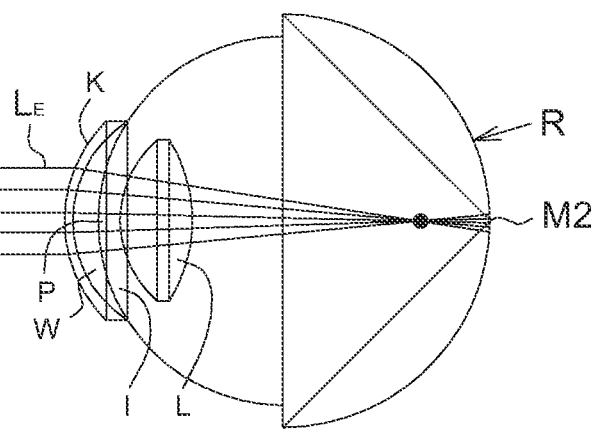
FIG. 15A illustrate an optical path of a light beam imitated according to a diagnostic equipment in FIG. 13 applied in a near-sighted eye tissue.
Figure 15B:
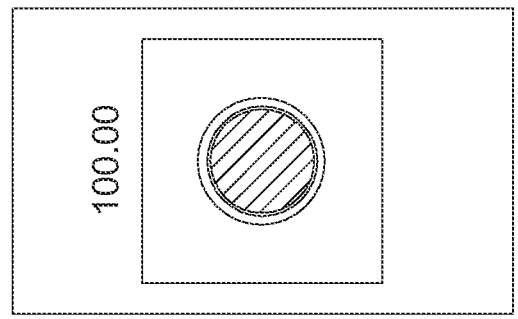
FIG. 15B illustrate a result of a focusing point on the retina in FIG. 15A.

FIG. 15A illustrates an imitation of the optical path of the light beam $L_E$ in the diagnostic equipment 7A' in FIG. 13 applying in the near sighted eye tissue E2 according to one embodiment of the disclosure. As shown in FIG. 15A, if the eyeball is a near sighted eyeball, the diameter of the eye tissue E2 is 25 mm and is larger than a standard one (take the eye tissue E1 as the standard eye tissue). The parameters of the cornea K to that of the eye lens L in the eye tissue E2 are the same as the parameters of the eye tissue E1. The light beam $L_E$ incident to the eye tissue E2 will not focus on the retina R, and the luminescent spot M2 becomes larger. As shown in FIG. 15A, when the light beam $L_E$ is incident to a near sighted eye tissue E2, the light beam $L_E$ is focused in front of the retina R. FIG. 15B illustrates the focusing point M2 on the retina R. The software of Zemax analyzes the retina R according to the imitating experiments in FIG. 15A, the focusing point M2 and the luminescent spot of RMS is 23.092 μm, the radius of the luminescent spot is 36.966 μm.

Figure 16A:
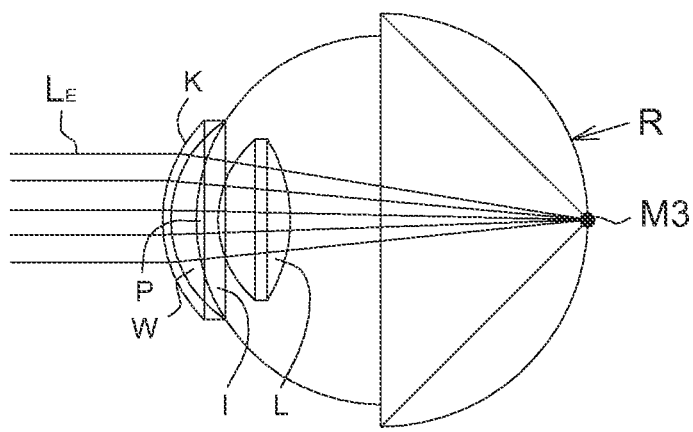
FIG. 16A illustrates an imitation of an optical path of an auto-focusing light beam applied in a near-sighted eye tissue with diagnostic equipment in FIG. 13.
Figure 16B:
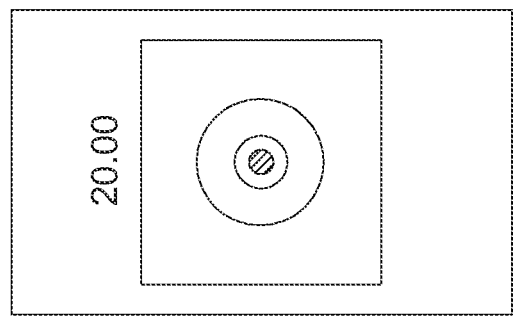
FIG. 16B illustrates a result of a focusing point on the retina in FIG. 16A.

FIG. 16A illustrates an imitation of the auto-focusing optical path of the light beam $L_E$ in the diagnostic equipment 7A' in FIG. 13 applying in the near sighted eye tissue E1 according to one embodiment of the disclosure. Please refer to FIG. 16A, when the auto-focusing function is activated in the focusing detection device, the mobile platform can move the ocular lens 148 in a direction toward the scan mirror 147 until the ocular lens 148 is in back of the focusing point and apart from the focusing point with a distance of 16.62 mm (a distance between the focusing point and the ocular lens 148 in FIG. 13 is 19.23 mm). In this time, the focusing status of the retina R of the near sighted eye tissue E2 and the focusing point M3 are shown in FIG. 16B. The light beam $L_E$ (such as a tomography light beam) focus on the retina R accurately again. Besides, the radius of the RMS of the focusing point M3 (Root mean square) decreases from 23.092 μm in FIG. 15B to 1.66 μm, this value is close to the radius of the RMS of the focusing point M1 in FIG. 14B (which is 1.58 μm). Besides, the geometry radius of the focusing point M3 is 5.50 μm, which is close to the geometry radius of the focusing point M1 on ordinary eye tissue E1 without near sighted in FIG. 14B (about 5.2 μm). That is to say, the diagnostic equipment 7A' can achieve the auto-focusing function.

Figure 17:
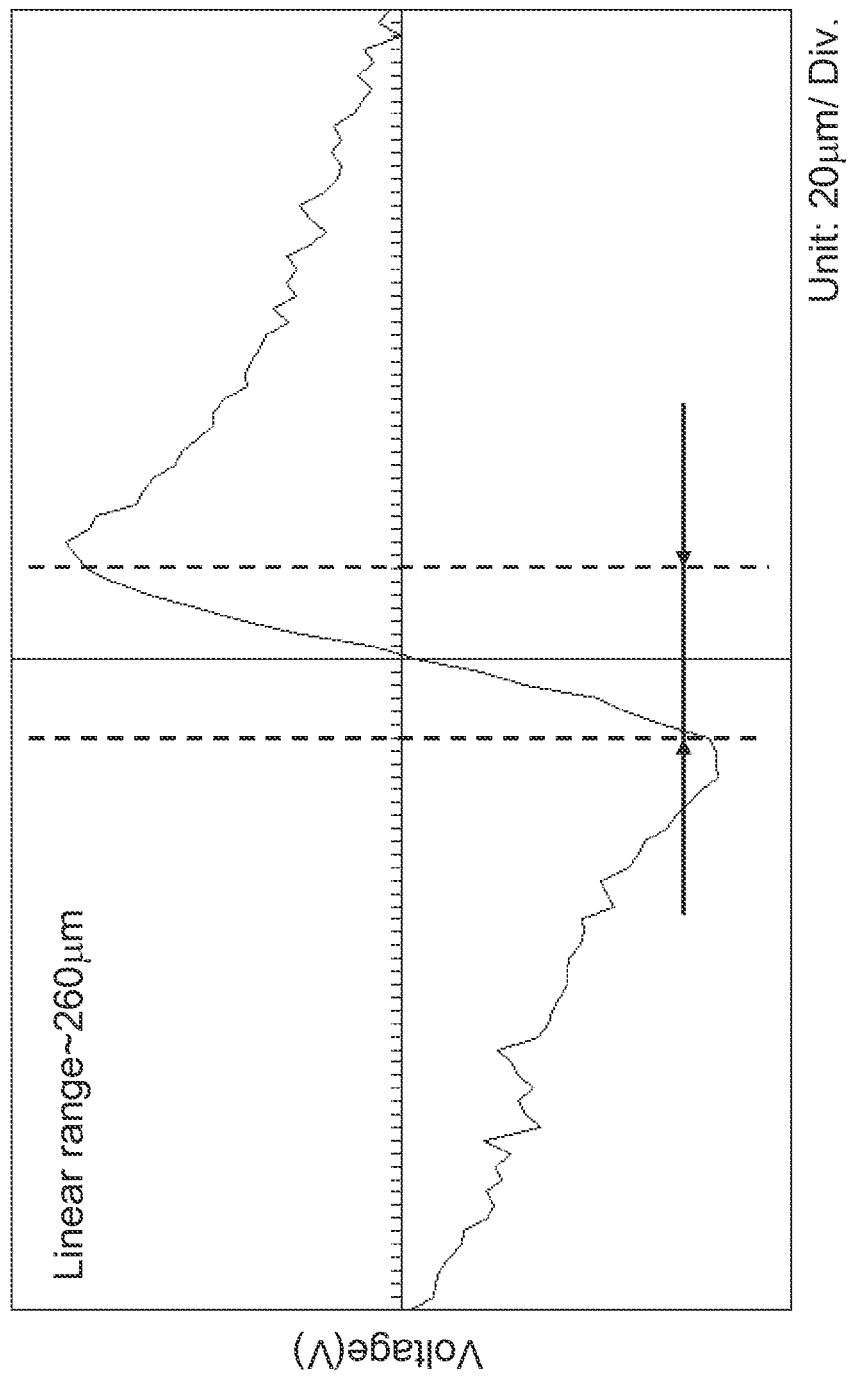
FIG. 17 illustrates a signal waveform diagram detected by a photo detector of the diagnostic equipment in FIG. 13.

FIG. 17 illustrates a signal waveform diagram detected by the photo detector according to the structure of the diagnostic equipment 7A' in FIG. 13. Please refer to both FIG. 13 and FIG. 17, whether the focusing position of the eye tissue E' is exactly on the retina R or not is undetermined in the diagnostic equipment 6A', before performing the measurement of eye tissue E'. At this time, the mobile platform (not shown) can control the ocular lens 148 moving back and forth automatically to scan the retina in the fundus. Then, the photo detector (not shown) obtains a defocus signal by performing the astigmatic method. The defocus signal is shown as the S shaped curve in FIG. 17.

As shown in FIG. 17, the unit of the vertical axis in the diagram is voltage (V), the unit of the horizontal axis in the diagram is 20 μm/Div. When the voltage level is equal to 0, the focusing point is located on the retina R accurately. The linear range of the S curve is about 260 μm. After the server system of the focusing detection device 12 is activated, the defocus signal can be compressed under 1/10 of a peak value of the defocus signal. In other words, the final focusing position error can be compressed below 26 μm (1/10 of a value of the peak value minus the valley value). Since the thickness of the ordinary OCT scanning device is about 2 mm, an error of 26 μm is acceptable.

Figure 18A:
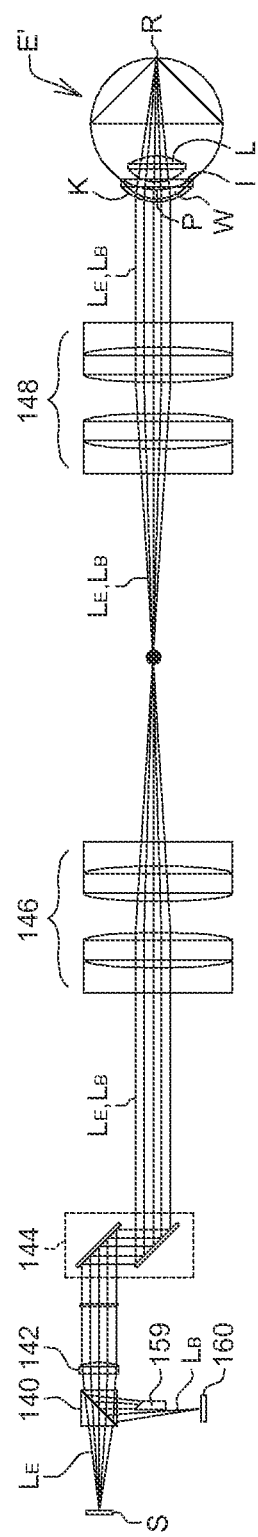
FIG. 18A illustrates an imitation of a diagnostic equipment imitated by Zemax imitate software according to an embodiment of the disclosure.
Figure 18B:
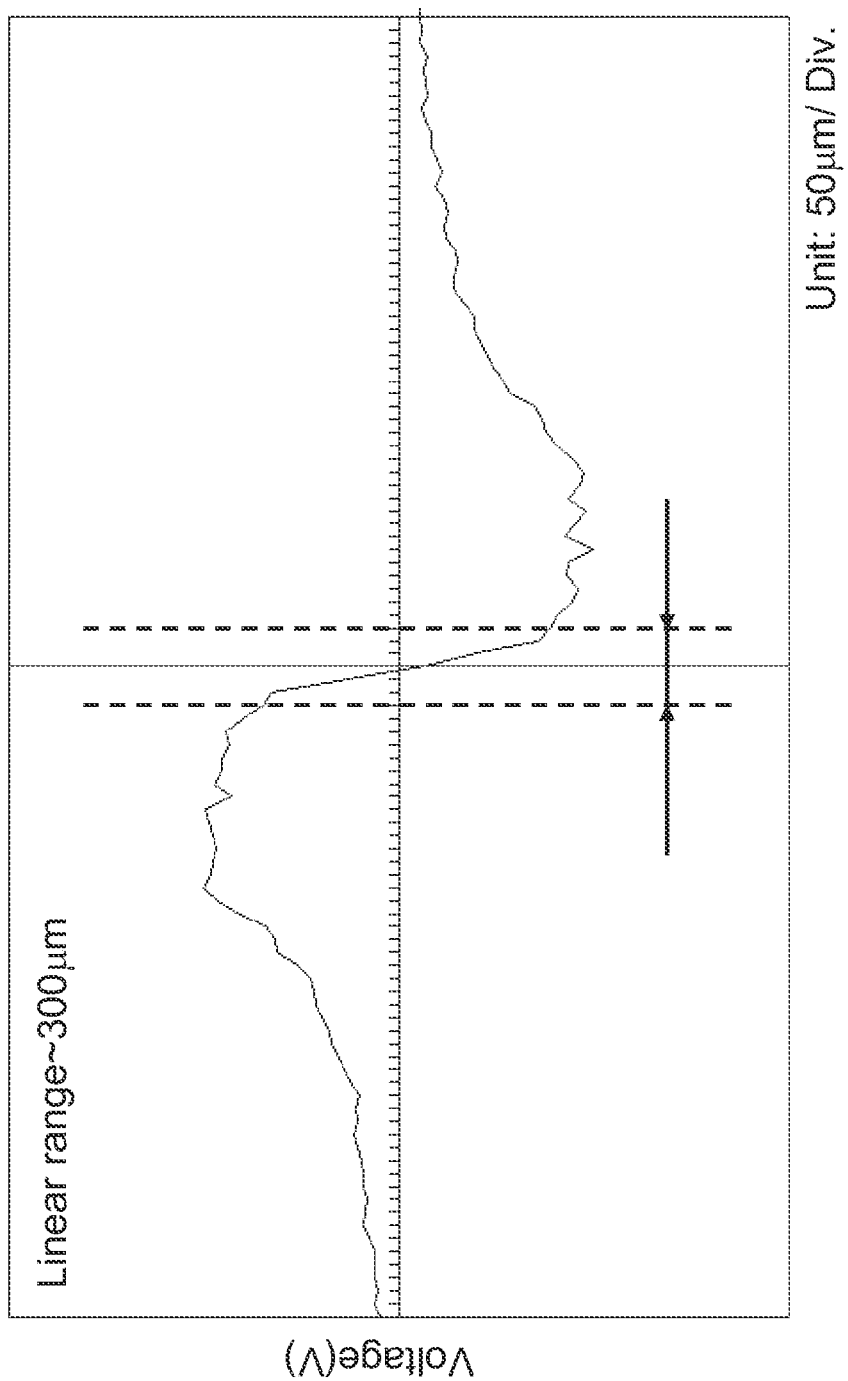
FIG. 18B illustrates a signal waveform diagram detected by a photo detector of the diagnostic equipment in FIG. 18A.

FIG. 18A illustrates an imitation diagram of the diagnostic equipment 8A' imitated by the Zemax software according to an embodiment of the disclosure. The light emitting path of the imitation structure in the diagnostic equipment 7A in FIG. 18A is similar to that of the diagnostic equipment 7A' in FIG. 13, the similarities are not repeatedly herein. The differences between the diagnostic equipment 8A' in FIG. 18A and the diagnostic equipment 7A' in FIG. 13 is that the light beam returning path in the diagnostic equipment 8A' utilizes a knife edge method. The knife edge method covers half of the light beam by disposing a blade 159 at a position in a distance of 8 mm below the beam splitter prism 140. In this embodiment, the photo detector 160 is a binary photo detector with a 60 μm square photo detector integrated circuit (PDIC). The distances between the division is 0.5 μm. The PDIC is disposed at a position in a distance of 6.82 mm below the blade 159. By moving the ocular lens 148 along the optical axis back and forth, the S curve of the defocus signal is illustrated in FIG. 18B. As shown in FIG. 18B, the vertical axis of the waveform diagram is voltage (V), and the unit of the horizontal axis in the diagram is 50 μm/Div. When the voltage level is equal to 0, the focusing point is located on the retina R accurately. The linear range of the S curve is about 300 μm. When the S curve is obtained by the server system of the diagnostic equipment 8A', the mobile platform (not shown) can move the ocular lens 148 to a position having a signal below 1/10 of the peak value of the defocus signal to complete the auto-focusing process.

Figure 19A:
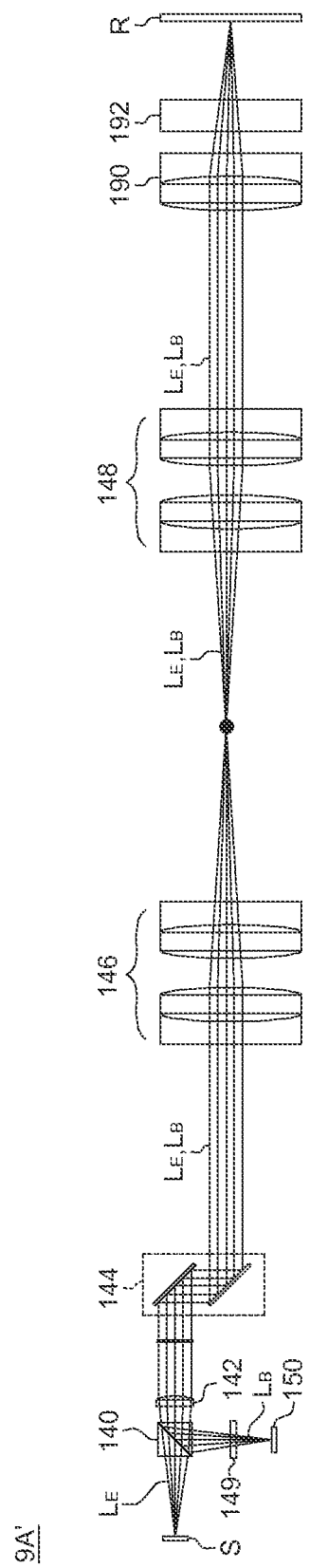
FIG. 19A illustrates an imitation of a diagnostic equipment imitated by Zemax imitate software according to an embodiment of the disclosure.

FIG. 19A illustrates an imitation diagram of the diagnostic equipment 9A' imitated by the Zemax software according to an embodiment of the disclosure. As shown in FIG. 19A, the laser light beam $L_E$ with a waveform of 780 nm is emitted and passes through a distance of 28.37 mm to be incident to a 6 mm splitter prism 140 (with a material of BK7). Then, the laser light beam $L_E$ passes through a distance of 3 mm and is incident to a flat convex glass spherical collimating mirror 142 having an outer diameter of 6.6 mm. At this time, the light beam $L_E$ becomes a parallel light beam. After the parallel light beam passes through a distance of 20 mm, the parallel light beam is incident to the scan mirror assembly 144. A distance between the centers of the two reflecting mirrors of the scan mirror assembly 144 is 9.7 mm. If the centers of the mirrors of the scan mirror assembly 144 is located at a central position, the light beam $L_E$ reflected by the mirrors is incident to the center of the scan mirror 147.

In this imitation, the mirror aplanat assembly in FIG. 13 is used as the scan mirror 147. The mirror parameters of the mirror aplanat assembly are not repeatedly herein. The laser light beam $L_E$ emitted from the scan mirror 147 is focused at a distance of 42.54 mm in back of the scan mirror 147. Then, the laser light beam $L_E$ is divergent and passes through a distance of 19.23 mm, and then the laser light beam $L_E$ is incident to the ocular lens 148.

In this imitation, another one pair of the mirror aplanat assembly is used. The mirror parameters of the another one pair of the mirror aplanat assembly is the same as that of the mirror aplanat assembly in FIG. 13, the similarities are not repeatedly herein. The laser light beam $L_E$ emitted from the ocular lens 148 and passes through the air with a distance of 56.44 mm is incident to the focusing lens assembly 190 (also refer to as the anterior chamber mirror assembly). The focusing lens assembly 190 is another one mirror aplanat assembly, and the mirror parameters such as the radius of curvature of the mirror aplanat assembly from the emitting direction of the light beam $L_E$ to the eye tissue to be examined are 26.12 mm, −21.28 mm and −137.09 mm. The thickness of the another one mirror aplanat assembly are 10 mm and 2.5 mm, respectively. The material of the another one mirror aplanat assembly are N-BAF10 and N-SF6, respectively. After the laser light beam $L_E$ emitting from anterior chamber mirror passes through the air for a distance of 5 mm, the laser light beam $L_E$ passes though a 4 mm glass 192 with a N-BK7 material. The glass 192 can protect the focusing lens assembly 190 and compensate the chromatic aberration. The laser light beam $L_E$ passes though a distance of 28.25 mm and is incident to the surface of the cornea R. Since the difference of refraction coefficient between the surface of the cornea R and air is large, a stronger reflected light signal can be generated. In one embodiment, the focusing lens assembly 190 and glass 192 can be integrated into a lens assembly.

After the reflected laser light beam $L_B$ passing through the anterior chamber mirror 190, most of the reflected laser light beam $L_B$ returns back along the original path and passes through the ocular lens 148, the scan mirror 147, the scan mirror assembly 144 in order. Then, the reflected laser light beam $L_B$ is incident to the collimating mirror 142 and a 6 mm beam splitter prism 140. At this time, parts of the light beam $L_B$ would be reflected and is incident to the cylindrical lens 149 at a distance of 24 mm below the beam splitter prism 140. Finally, the light beam $L_B$ passes through a distance of 4.50 mm and is incident to a quad-division photo detector 150. The cylindrical lens 149 and the photo detector 150 are the same as that in FIG. 13, the similarities are not repeatedly here.

Figure 19B:
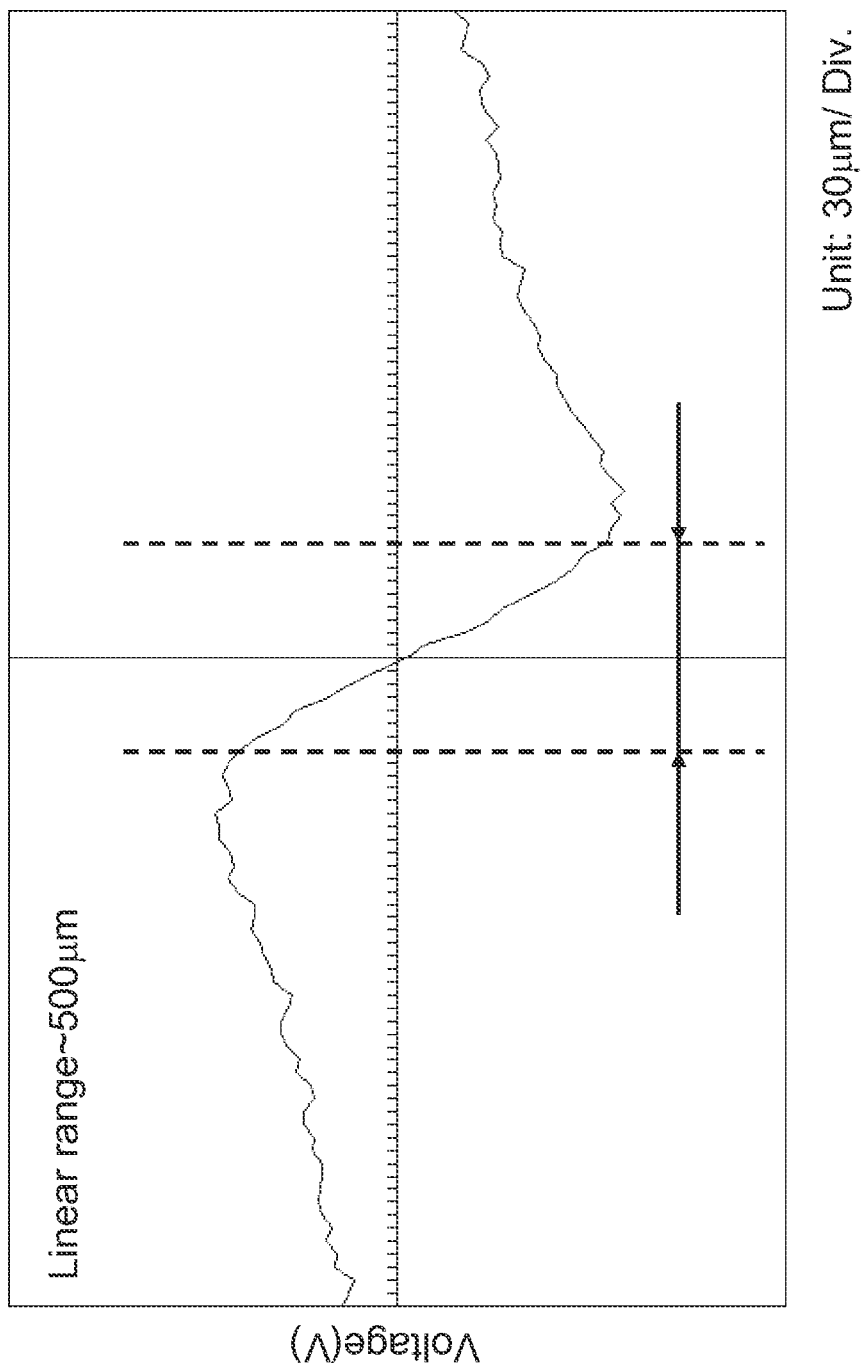
FIG. 19B illustrates a signal waveform diagram detected by a photo detector of the diagnostic equipment in FIG. 19A.

FIG. 19B illustrates a defocus signal according to the diagnostic equipment 9A' in FIG. 19A having a mobile platform that controls the movement of the focusing lens 190 along the optical axis back and forth. As shown in FIG. 19B, the unit of the vertical axis of the waveform diagram is voltage (V), and the unit of the horizontal axis of the waveform diagram is 30 μm/Div. When the voltage is equal to 0, the focusing point can focus on the retina R accurately. The defocus signal is represented by curve S having a linear range, and the length of the linear range is about 500 μm.

Figure 20A:
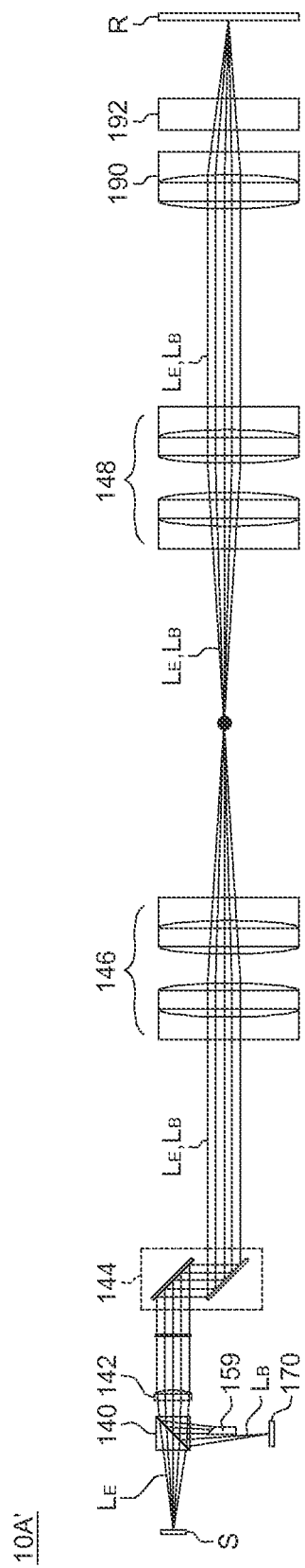
FIG. 20A illustrates an imitation of a diagnostic equipment imitated by Zemax imitate software according to an embodiment of the disclosure.

FIG. 20A illustrates an imitation diagram of the diagnostic equipment 10A' imitated by the Zemax software according to an embodiment of the disclosure. The optical path of the imitated construction of the diagnostic equipment 10A in FIG. 20A is similar to the optical path of the diagnostic equipment 9A' in FIG. 19A, and the similarities are not repeated herein. The difference between the diagnostic equipment 10A in FIG. 20A and the diagnostic equipment 9A' in FIG. 19A is that the returning optical path of the diagnostic equipment 10A in FIG. 20A can be analyzed by ways of a knife edge method. The blade 159 is disposed in a distance of 8 mm below the beam splitter prism 140 to cover half of the light beam. In this embodiment of the experiment, the photo detector 170 is a binary photo detector with a square PDIC having a width of 60 μm. The distance between the divisions is 0.5 μm. The photo detector 170 is disposed in a distance of 15.29 mm below the blade 159. A defocus signal can be obtained by moving the focusing lens 190 along the optical axis back and forth, and the defocus signal is illustrated as the curve S in FIG. 20B.

Figure 20B:
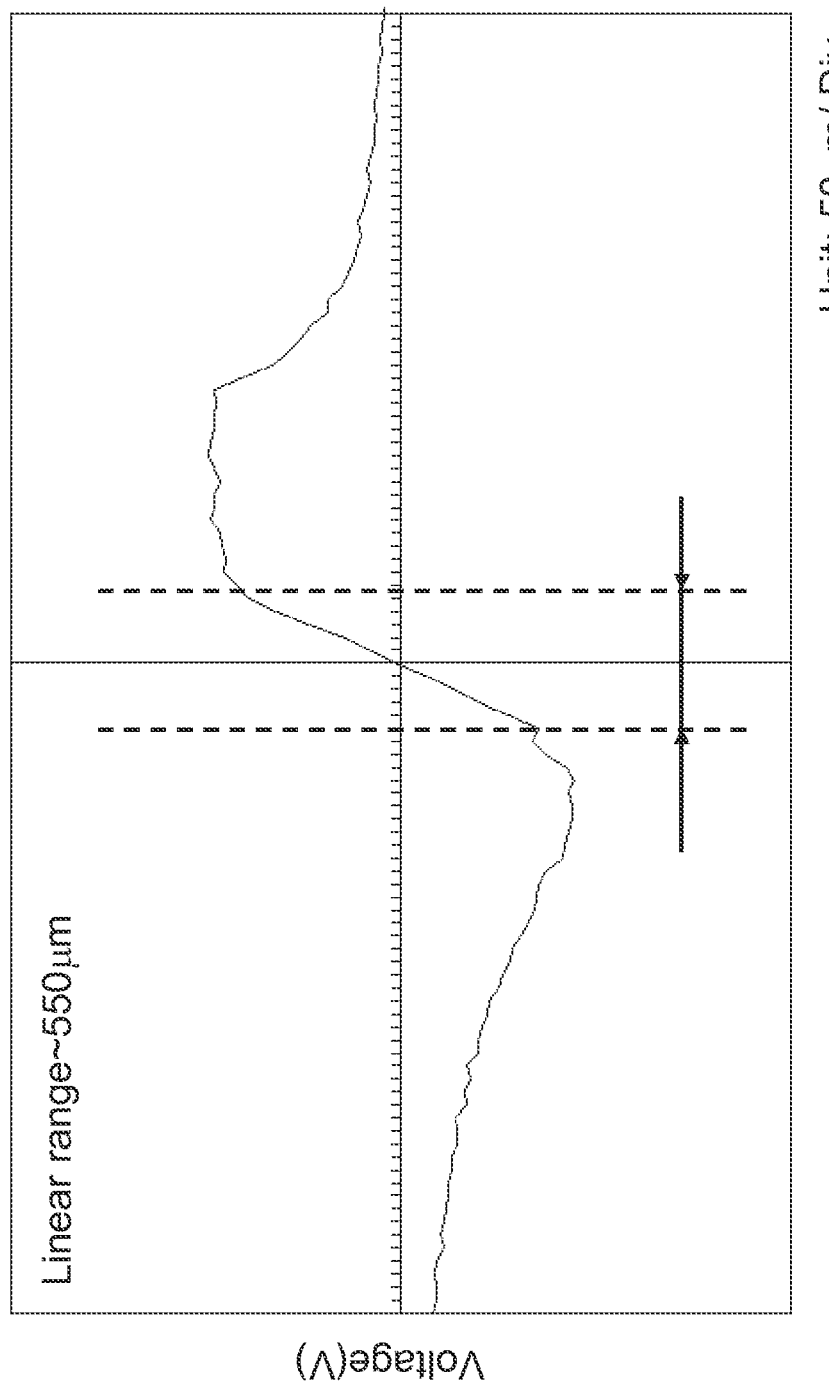
FIG. 20B illustrates a signal waveform diagram detected by a photo detector of the diagnostic equipment in FIG. 19A.

As shown in FIG. 20B, the unit of the vertical axis of the waveform diagram is voltage (V), and the unit of the horizontal axis of the waveform diagram is 50 μm/Div. When the voltage is 0, the focusing point is located on the retina R accurately. The S curve of the defocus signal has a linear range. The length of the linear range is about 550 μm. After the S curve obtained by the server system of the diagnostic equipment 10A', the mobile platform (not illustrate) can control the focusing lens 190 to move, so that the defocus signal can be compressed to less than 1/10 of the original peak value of the defocus signal. At this time, the auto-focusing process is completed. The largest error is 55 μm and is neglectable with respect to the 2 mm scanning thickness of the OCT.

Based on the above, a defocus level between the mobile optical lens assembly and splitter assembly and a corresponding signal can be determined by the focusing detection device and focus detecting method in the described embodiments. Besides, the control module can move the mobile optical lens assembly to adjust a distance between the mobile optical lens assembly and splitter assembly according to the signal, so that the light beam of the focusing detection device can focus on the cornea K, the anterior chamber W, the eye lens L or the retina R of the eye tissue accurately. Since the light beam provided by the light source of the tomography device, the light source of the fundoscope and the light source of the focusing detection device can focus on the cornea K, the anterior chamber W, the eye lens L or the retina R through the lens of the splitter assembly and the lens of the mobile optical lens assembly. When a distance between the splitter assembly and lens enables the light beam $L_{f3}$ can focus on the cornea K, the anterior chamber W, the eye lens L or the retina R accurately, the light beam $L_{f1}$ and the light beam $L_{f2}$ can also focus on the cornea K, the anterior chamber W, the eye lens L or the retina R accurately. Therefore, the auto-focusing process of the tomography device and the fundoscope can be completed.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A diagnostic equipment having an auto-focusing function, comprising:
   a image detection device comprising a first light source and a first photo detector, the first light source providing a first incident light, the first incident light incident to an object and becoming a first signal light, the first photo detector used for receiving the first signal light;
   a first scanning device for adjusting a path of the first incident light and to scan the object;
   a mobile optical lens assembly having a lens and a mobile platform for carrying the lens;
   a focusing detection device comprising:
   a second photo detector used for detecting a second signal light reflected by the object, wherein the second signal light is a defocus signal;
   a focusing error produce assembly disposed between the second photo detector and the mobile optical lens assembly; and
   a controlling unit being electrical connected to the second photo detector and the mobile platform to control a movement of the mobile platform and adjust a focusing position of the first incident light according to an electric signal converted by the second signal light; and
   a first splitter assembly used for transmitting the first signal light to the first photo detector and transmitting the second signal light to the second photo detector.

2. The diagnostic equipment according to claim 1, wherein the lens of the mobile optical lens assembly is a focusing lens, and the diagnostic equipment further comprises a ocular lens disposed between the first scanning device and the mobile optical lens assembly.

3. The diagnostic equipment according to claim 1, further comprising a optical fiber and a first collimating mirror disposed between the first light source and the first scanning device.

4. The diagnostic equipment according to claim 2, further comprising a optical fiber and a first collimating mirror disposed between the first light source and the first scanning device.

5. The diagnostic equipment according to claim 1, wherein the focusing detection device further comprising a second light source and a second splitter assembly, wherein the second light source used for providing a second incident light, the second incident light is incident to the object through the second splitter assembly and reflected by an object and becomes the second signal light.

6. The diagnostic equipment according to claim 2, wherein the focusing detection device further comprising a second light source and a second splitter assembly, wherein the second light source used for providing a second incident light, the second incident light is incident to the object through the second splitter assembly and reflected by the object and becomes the second signal light.

7. The diagnostic equipment according to claim 1, wherein the second signal light is a signal provided by the first signal light.

8. The diagnostic equipment according to claim 2, wherein the second signal light is a signal provided by the first signal light.

9. The diagnostic equipment according to claim 1, wherein the first scanning device comprise a first scan mirror and a first scan assembly, the first scan assembly is a pair of scanning reflecting mirrors.

10. The diagnostic equipment according to claim 2, wherein the first scanning device comprises a first scan mirror and a first scan assembly, the first scan assembly is a pair of scanning reflecting mirrors.

11. The diagnostic equipment according to claim 1, wherein the image detection device is a tomography device, the first light source comprise a tomography light source, the first photo detector is a spectrometer, the first incident light is reflected by the object and becomes the first signal light.

12. The diagnostic equipment according to claim 2, wherein the image detection device is a tomography device, the first light source comprise a tomography light source, the first photo detector is a spectrometer, the first incident light is reflected by the object and becomes the first signal light.

13. The diagnostic equipment according to claim 1, the image detection device is a fundoscope, the first light source is a fundoscope light source, the object is an eye tissue, the first photo detector is a image module used for displaying a image signal converted from the first signal light.

14. The diagnostic equipment according to claim 1, wherein the first photo detector is a charge coupling diode, a complementary metal oxide semiconductor, PIN detector or avalanche photo detector.

15. The diagnostic equipment according to claim 2, wherein the first photo detector is a charge coupling diode, a complementary metal oxide semiconductor, PIN detector or avalanche photo detector.

16. The diagnostic equipment according to claim 1, wherein the image detection device comprise a tomography device and a fundoscope, the first light source comprise a tomography light source and a fundoscope light source, the first photo detector comprise a spectrometer and a image module, the first incident light is reflected by the object and becomes the first signal light.

17. The diagnostic equipment according to claim 13, further comprising a second scan device disposed between the fundoscope light source and the mobile optical lens assembly, wherein the second scan device is used for adjust a optical path of the fundoscope light source to scan the eye tissue.

18. The diagnostic equipment according to claim 16, further comprising a second scan device disposed between the fundoscope light source and the mobile optical lens assembly, wherein the second scan device is used for adjust a optical path of the fundoscope light source to scan an eye tissue.

19. The diagnostic equipment according to claim 17, wherein the second scan device comprise a second scan assembly and a second scan mirror, the second scan assembly is another pair of scanning reflecting mirrors.

20. The diagnostic equipment according to claim 18, wherein the second scan device comprise a second scan assembly and a second scan mirror, the second scan assembly is another pair of scanning reflecting mirrors.

21. The diagnostic equipment according to claim 1, wherein the image detection device comprises a tomography device and a fundoscope, the first light source comprises a tomography light source or a fundoscope light source, the first photo detector comprises a spectrometer and a image module, the first incident light is reflected by the object and becomes the first signal light.

22. The diagnostic equipment according to claim 1, wherein the focusing error produce assembly is a light transmissive plate, the focusing detection device further comprises a second collimating mirror, the second collimating mirror is disposed between the mobile optical lens assembly and the second photo detector, and the light transmissive plate is disposed between the second collimating mirror and the second photo detector slantly.

23. The diagnostic equipment according to claim 22, wherein the focusing detection device further comprises a second light source and a second splitter assembly, the second light source is used for providing a second incident light, the second incident light is reflected by the object and becomes the second signal light, the second splitter assembly is disposed between the second light source and the second photo detector and the second collimating mirror.

24. The diagnostic equipment according to claim 1, wherein the focusing error produce assembly is a cylindrical lens, the focusing detection device further comprises a second collimating mirror, the cylindrical lens and the second collimating mirror are disposed between the mobile optical lens assembly and the second photo detector, and the cylindrical lens is disposed between the second collimating mirror and the second photo detector.

25. The diagnostic equipment according to claim 24, wherein the focusing detection device further comprises a second light source and a second splitter assembly, the second light source is used for provide a second incident light, the second incident light reflected by the object and becomes the second signal light, the second splitter assembly is disposed between the second collimating mirror and the cylindrical lens.

26. The diagnostic equipment according to claim 1, wherein the focusing error produce assembly is a blade, the focusing detection device further comprise a second collimating mirror, the second collimating mirror is disposed between the mobile optical lens assembly and the second photo detector, and the blade is disposed between the second collimating mirror and the second photo detector.

27. The diagnostic equipment according to claim 26, wherein the focusing detection device further comprises a second light source and a second splitter assembly, the second light source used for providing a second incident light, the second incident light is reflected by the object and becomes the second signal light, the second splitter assembly is disposed between the second collimating mirror and the blade.

28. The diagnostic equipment according to claim 1, wherein the focusing error produce assembly is a second splitter assembly and a third photo detector, the focusing detection device further comprises a second collimating mirror, the second collimating mirror is disposed between the mobile optical lens assembly and the second photo detector, and the second splitter assembly is disposed between the second collimating mirror and the second photo detector, and the second photo detector and the third photo detector are respectively disposed between two light emitting surfaces of the second splitter assembly.

29. The diagnostic equipment according to claim 28, wherein the focusing detection device further comprises a second light source a third splitter assembly, the second light source is disposed at a light incident surface of the third splitter assembly, the third splitter assembly is disposed between the second splitter assembly and the mobile optical lens assembly.

30. The diagnostic equipment according to claim 2, wherein the mobile platform further carries the ocular lens.

31. The diagnostic equipment according to claim 2, wherein the mobile platform further carries the ocular lens and the first scanning device.

32. The diagnostic equipment according to claim 30, wherein the first splitter assembly is disposed at a side away from the mobile optical lens assembly of the first scanning device.

33. The diagnostic equipment according to claim 31, wherein the first splitter assembly is disposed at a side away from the mobile optical lens assembly of the first scanning device.

* * * * *

UNITED STATES PATENT AND TRADEMARK OFFICE
CERTIFICATE OF CORRECTION

PATENT NO. : 8,894,206 B2
APPLICATION NO. : 13/727664
DATED : November 25, 2014
INVENTOR(S) : Lee et al.

It is certified that error appears in the above-identified patent and that said Letters Patent is hereby corrected as shown below:

On the title page, Item (30) please replace the foreign application priority number of "201210411541" with "201210411541.4"

Signed and Sealed this
Nineteenth Day of May, 2015

Michelle K. Lee
*Director of the United States Patent and Trademark Office*